United States Patent
Kovalski et al.

(10) Patent No.: US 10,209,376 B2
(45) Date of Patent: Feb. 19, 2019

(54) SYSTEMS FOR IMAGE DETECTION

(71) Applicant: General Electric Company, Schenectady, NY (US)

(72) Inventors: Gil Kovalski, Haifa (IL); Jean-Paul Bouhnik, Zichron Yaacov (IL); Jonathan Sachs, Haifa (IL); Yariv Grobshtein, Haifa (IL); Yulim Zingerman, Netanya (IL); Arie Eshco, Haifa (IL); Yaron Hefetz, Tirat Carmel (IL)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/905,266

(22) Filed: Feb. 26, 2018

(65) Prior Publication Data

US 2018/0188393 A1 Jul. 5, 2018

Related U.S. Application Data

(63) Continuation of application No. 15/431,141, filed on Feb. 13, 2017, now Pat. No. 9,903,962, which is a
(Continued)

(51) Int. Cl.
*G01T 1/166* (2006.01)
*G01T 1/29* (2006.01)
(Continued)

(52) U.S. Cl.
CPC ............ *G01T 1/2985* (2013.01); *A61B 6/037* (2013.01); *A61B 6/4258* (2013.01);
(Continued)

(58) Field of Classification Search
CPC ....... G01T 1/1648; G01T 1/166; G01T 1/161; G01T 1/2985; G06T 11/005
See application file for complete search history.

(56) References Cited

U.S. PATENT DOCUMENTS 3,774,031 A 11/1973 Mallard et al.
4,204,123 A 5/1980 Stoddart
(Continued)

FOREIGN PATENT DOCUMENTS

EP 2275989 A1 1/2011
JP 10-160848 A 6/1998
(Continued)

OTHER PUBLICATIONS

Non-Final Office Action issued in connection with related U.S. Appl. No. 14/501,337 dated May 1, 2015 (9 pages).
(Continued)

*Primary Examiner* — Kiho Kim
(74) *Attorney, Agent, or Firm* — Dean D. Small; The Small Patent Law Group, LLC

(57) ABSTRACT

A customizable and upgradable imaging system is provided. Imaging detector columns are installed in a gantry to receive imaging information about a subject. Imaging detector columns can extend and retract radially as well as be rotated orbitally around the gantry. The gantry can be partially populated with detector columns and the detector columns can be partially populated with detector elements.

18 Claims, 23 Drawing Sheets

Related U.S. Application Data continuation of application No. 14/925,148, filed on Oct. 28, 2015, now Pat. No. 9,606,247, which is a continuation of application No. 14/612,398, filed on Feb. 3, 2015, now Pat. No. 9,213,110, which is a continuation of application No. 14/135,751, filed on Dec. 20, 2013, now Pat. No. 9,029,791.

(51) Int. Cl.

| | | |
|---|---|---|
| *G06T 11/00* | (2006.01) | |
| *G01T 1/164* | (2006.01) | |
| *A61B 6/03* | (2006.01) | |
| *A61B 6/00* | (2006.01) | |
| *G01T 1/161* | (2006.01) | |

(52) U.S. Cl.
CPC ............ *A61B 6/4266* (2013.01); *G01T 1/161* (2013.01); *G01T 1/166* (2013.01); *G01T 1/1648* (2013.01); *G06T 11/005* (2013.01); *A61B 6/503* (2013.01); *A61B 6/545* (2013.01); *A61B 6/547* (2013.01)

(56) References Cited

U.S. PATENT DOCUMENTS

| | | | |
|---|---|---|---|
| 5,047,641 | A | 9/1991 | Besseling et al. |
| 5,252,830 | A | 10/1993 | Weinberg |
| 5,436,958 | A | 7/1995 | Taylor |
| 5,594,251 | A | 1/1997 | Fleury et al. |
| 5,675,513 | A | 10/1997 | Hammer |
| 5,689,543 | A | 11/1997 | Graves et al. |
| 5,717,212 | A | 2/1998 | Fulton et al. |
| 5,949,842 | A | 9/1999 | Schafer et al. |
| 6,043,494 | A | 3/2000 | Yamakawa et al. |
| 6,114,701 | A | 9/2000 | Plummer et al. |
| 6,147,353 | A | 11/2000 | Gagnon et al. |
| 6,256,404 | B1 | 7/2001 | Gordon et al. |
| 6,271,524 | B1 | 8/2001 | Wainer et al. |
| 6,279,420 | B1 | 8/2001 | Knorowski et al. |
| 6,636,214 | B1 | 10/2003 | Leather et al. |
| 7,223,240 | B2 | 5/2007 | Murashita |
| 7,280,638 | B1 | 10/2007 | Weaver et al. |
| 7,555,164 | B2 | 6/2009 | Kim |
| 7,592,597 | B2 | 9/2009 | Hefetz et al. |
| 7,601,966 | B2 | 10/2009 | Ben-Haim |
| 7,705,316 | B2 | 4/2010 | Rousso et al. |
| 7,829,856 | B2 | 11/2010 | Jansen et al. |
| 8,194,237 | B2 | 6/2012 | Cronin et al. |
| 8,338,788 | B2 | 12/2012 | Zilberstein et al. |
| 8,421,021 | B2 | 4/2013 | Sachs et al. |
| 8,479,213 | B2 | 7/2013 | Jones et al. |
| 8,487,265 | B2 | 7/2013 | Heukensfeldtjansen et al. |
| 8,492,725 | B2 | 7/2013 | Zilberstein et al. |
| 8,542,892 | B2 | 9/2013 | Kovalski |
| 8,542,898 | B2 | 9/2013 | Bathe et al. |
| 8,575,555 | B2 | 11/2013 | Wangerin et al. |
| 8,610,075 | B2 | 12/2013 | Rousso et al. |
| 8,748,827 | B2 | 6/2014 | Zilberstein et al. |
| 9,182,507 | B2 | 11/2015 | Hefetz et al. |
| 9,295,439 | B2 | 3/2016 | Hefetz |
| 9,297,913 | B2 | 3/2016 | Grobshtein et al. |
| 9,392,981 | B2 | 7/2016 | Khen et al. |
| 9,439,607 | B2 | 9/2016 | Khen et al. |
| 9,662,079 | B2 | 5/2017 | Rafaeli et al. |
| 2004/0195512 | A1* | 10/2004 | Crosetto ................ A61B 6/037 250/363.04 |
| 2004/0262525 | A1 | 12/2004 | Yunker et al. |
| 2008/0001090 | A1 | 1/2008 | Ben-Haim |
| 2008/0029704 | A1 | 2/2008 | Hefetz et al. |
| 2010/0001190 | A1 | 1/2010 | Wleczorek et al. |
| 2010/0121604 | A1 | 5/2010 | Vaisburd |
| 2013/0120200 | A1 | 2/2011 | Zilberstein |
| 2012/0248320 | A1 | 10/2012 | Wangerin et al. |
| 2013/0123602 | A1 | 5/2013 | Kovalski et al. |
| 2013/0320234 | A1 | 12/2013 | Volokh et al. |
| 2014/0343412 | A1 | 11/2014 | Wieczorek et al. |
| 2015/0065873 | A1 | 3/2015 | Tsukerman et al. |
| 2015/0094573 | A1* | 4/2015 | Bouhnik ............... G01T 1/2985 600/427 |
| 2015/0119704 | A1 | 4/2015 | Roth et al. |

FOREIGN PATENT DOCUMENTS

| | | |
|---|---|---|
| JP | 2008-039776 A | 2/2008 |
| WO | 2014165472 A1 | 10/2014 |

OTHER PUBLICATIONS

Non-Final Office Action issued in connection with related U.S. Appl. No. 14/501,337 dated Jun. 11, 2015 (8 pages).

Non-Final Office Action issued in connection with related U.S. Appl. No. 14/327,178 dated Sep. 17, 2015 (6 pages).

Non-Final Office Action issued in connection with related U.S. Appl. No. 14/818,473 dated Mar. 17, 2016 (9 pages).

Divine; "Information Disclosure Statement" corresponding with related U.S. Appl. No. 14/925,148 (now U.S. Pat. No. 9,606,247). dated Oct. 28, 2015, (5 pages).

Conklin; "Information Disclosure Statement" corresponding with related U.S. Appl. No. 14/925,148 (now U.S. Pat. No. 9,606,247). dated Apr. 12, 2016, (6 pages).

"Notice of References Cited" corresponding with related U.S. Appl. No. 14/925,148 (now U.S. Pat. No. 9,606,247); (1 page).

"Notice of References Cited" corresponding with related U.S. Appl. No. 14/612,398 (now U.S. Pat. No. 9,213,110); (1 page).

132 S.Ct. 1289 (2012), "*Mayo Collaborative v. Prometheus Labs.*", pp. 1289-1305 (17 pages).

573 U. S. (2014), "*Alice Corp. v. CLS Bank Int'*", Syllabus, No. 13-298. October Term, 2013 (21 pages).

JP Notice of Preliminary Rejection for corresponding JP application No. 2016-541063 dated Jun. 26, 2018; 4 pages.

* cited by examiner

SYSTEMS FOR IMAGE DETECTION

CROSS-REFERENCE TO RELATED APPLICATION

The present application is a continuation of and claims priority to U.S. patent application Ser. No. 15/431,141 filed Feb. 13, 2017, titled "SYSTEMS FOR IMAGE DETECTION" which is a continuation of and claims priority to U.S. patent application Ser. No. 14/925,148 filed Oct. 28, 2015, titled "SYSTEMS FOR IMAGE DETECTION" which is continuation of and claims priority to U.S. Pat. No. 9,213,110 filed Feb. 3, 2015, titled "IMAGING SYSTEM USING INDEPENDENTLY CONTROLLABLE DETECTORS" which is a continuation of and claims priority to U.S. Pat. No. 9,029,791 filed Dec. 20, 2013, titled "IMAGING SYSTEM USING INDEPENDENTLY CONTROLLABLE DETECTORS", the disclosures of each of which are incorporated herein.

BACKGROUND

The subject matter disclosed herein relates generally to medical imaging systems, and more particularly to Nuclear Medicine (NM) imaging systems which can be Single Photon Emission Computed Tomography (SPECT) imaging systems.

In NM imaging, such as SPECT imaging, radiopharmaceuticals are administered internally to a patient. Detectors (e.g., gamma cameras), typically installed on a gantry, capture the radiation emitted by the radiopharmaceuticals and this information is used to form images. The NM images primarily show physiological function of, for example, the patient or a portion of the patient being imaged.

Conventional SPECT imaging systems include one, two or three gamma cameras mounted to a single gantry. These systems are generally not physically reconfigurable. The gamma cameras (also referred to as heads) are formed from particular materials. In the selection of material, tradeoffs must be made, such as imaging sensitivity, size, cost, etc. Additionally, specific collimation may be provided, which typically limits the application of the scanner to a particular type of scan, such as whole body bone exams, cardiac exams, etc. Thus, conventional SPECT imaging systems have limitations in design and/or operational characteristics. Moreover, there is limited flexibility in these imaging systems. There is a need for flexibility of an imaging system to be customizable based on specific patient need and operator cost constraints. There is also a need for imaging systems to automatically adjust imaging operations in systems that have changes in configurations.

BRIEF DESCRIPTION

In accordance with an embodiment, an adaptive imaging system is provided that includes a gantry, a plurality of imaging detector units installed in the gantry, at least some of the plurality of detector units movable relative to the gantry to position one or more of the detector units with respect to a subject, a controller configured to control the independent position of each detector unit, and wherein the controller adaptively alters at least one detector unit position for an imaging operation upon receiving installation information. The controller can be configured to develop an image acquisition scenario based the installation information and a requested imaging operation, configure a physical position of a least one detector unit installed in the gantry based on the developed image acquisition scenario, and acquire image information from the detector units.

DETAILED DESCRIPTION

Figure 1:
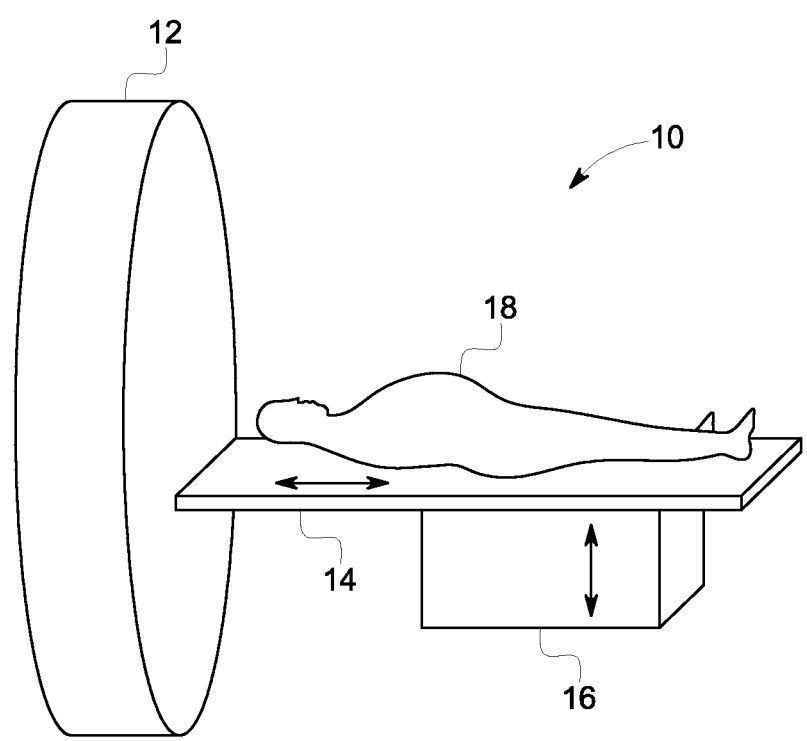
FIG. 1 is a perspective view of an exemplary medical imaging system.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide a medical imaging system, and in particular, a Nuclear Medicine (NM) imaging system having a gantry with a plurality of different types of imaging detectors mounted thereto. For example, in various embodiments of an NM imaging system, a Single Photon Emission Computed Tomography (SPECT) imaging scanner is provided that includes a plurality of detectors with a combination of different types of detectors that acquire SPECT image information. The various embodiments may include detectors formed from different materials, having different configurations or arrangements, having different collimation, etc. The system may be configured to perform single isotope or multi-isotope imaging.

It should be noted that although the various embodiments are described in connection with a particular NM imaging system, such as a SPECT detector system, the various embodiments may be implemented in connection with other imaging systems, such as a Positron Emission Tomography (PET) imaging system. Additionally, the imaging system may be used to image different objects, including objects other than people.

A medical imaging system 10 may be provided as illustrated in FIG. 1. A subject 18 can be a human patient in one embodiment. It should be noted that the subject 18 does not have to be human. It can be some other living creature or inanimate object in various embodiments. The subject 18 can be placed on a pallet 14 that can move a subject horizontally for locating the subject in the most advantageous imaging position. The bed mechanism 16 can raise and lower the pallet 14 vertically for locating the subject in the most advantageous imaging position. The gantry 12 is shown as circular in one embodiment. In other embodiments the gantry 12 may be of any shape such as square, oval, "C" shape, or hexagonal.

Figure 2:
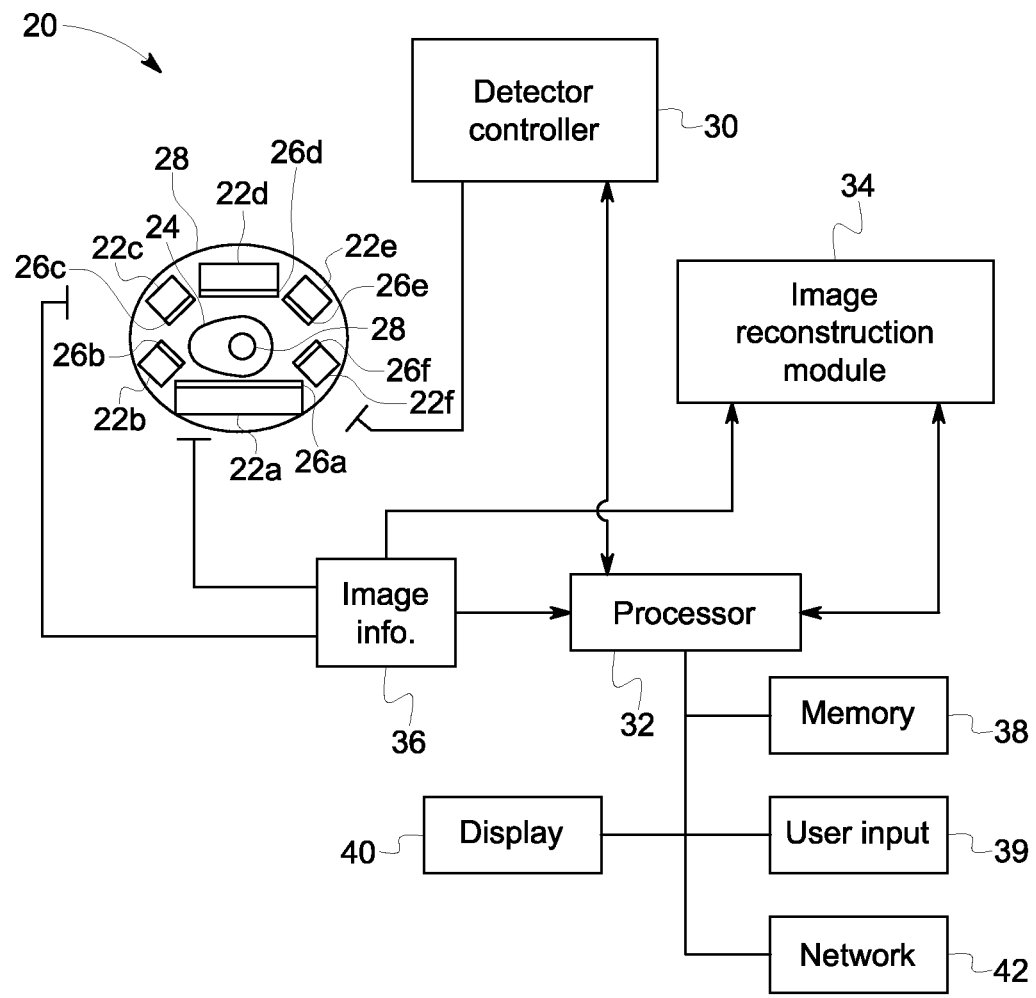
FIG. 2 is a simplified schematic block diagram illustrating a medical imaging system.

FIG. 2 shows the medical imaging system 20 in accordance with another embodiment. The medical imaging system 20 may be provided having a plurality of NM cameras configured as SPECT detector columns 22a-22f. It should be noted that the various embodiments are not limited to the medical imaging system 20 having six detector columns 22 as shown or to the sizes or shapes of the illustrated detector columns 22. For example, the medical imaging system 20 may include more or less detector columns 22 having different shapes and/or sizes, or formed from different materials. The medical imaging system 20 in various embodiments is configured as a hybrid SPECT system having a plurality of detector columns 22, wherein at least two of the detectors are formed from different materials, have different configurations or arrangements, have different collimation, or are otherwise different. Detector columns can be called detector units in some embodiments.

In operation, a subject, such as a patient 24, is positioned in proximity to the one or more of the detector columns 22 for imaging. The imaging system 20 can then re-adjust the detector columns 22 further from or closer to the patient 24 or patient area of interest as needed, which is heart 28 in an example embodiment. Imaging of the patient 24 is performed by one or more of the detector columns 22. The imaging by each of the detector columns 22 may be performed simultaneously, concurrently, or sequentially.

The position of the detector columns 22 may be varied, including the relative position between detector columns 22, tilt, angle, swivel, etc. of the detector columns 22. Additionally, each of the detector columns 22 may have a corresponding collimator 26a-26f mounted or coupled thereto. The collimators 26a-26f likewise may be of different types. One or more detector columns 22 may be coupled to a different type of collimator 26 (e.g., parallel hole, pin-hole, fan-beam, cone-beam, etc.). Accordingly, in various embodiments, the detector column 22 wholly includes collimator 26.

The detector columns 22 may include single crystal, or multi-crystal, detectors or pixelated detectors or scintillator based detectors that are configured to acquire SPECT image data. For example, the detector columns 22 may have detector elements formed from different materials, such as semiconductor materials, including Cadmium Zinc Telluride (CdZnTe), often referred to as CZT, Cadmium Telluride (CdTe), and Silicon (Si), among others, or non-semiconductor scintillator materials such as different types of crystal scintillators, for example, Sodium Iodide (NaI), Bismuth Germanate (BGO), Cerium-doped Lutetium Yttrium Orthosilicate (LYSO), Gadolinium Oxyorthosilicate (GSO), Cesium Iodide (CsI), Lanthanum (III) bromide ($LaBr_3$), among others. Additionally suitable components may be provided. For example, the detector columns 22 may be coupled to photosensors, such as an array of Photo-Multiplier Tubes (PMTs), an Avalanche Photodiode Detector (AFD), etc.

The imaging system 20 can also include a detector controller 30 that operates to control the movement of the detector columns 22 and/or the collimators 26. For example, the detector controller 30 may control movement of the detector columns 22, such as to rotate or orbit the detector columns 22 around a patient 24, and which may also include moving the detectors closer or farther from the patient 24 and pivoting/swiveling the detector columns 22, such that more localized movements or motions are provided. The detector controller 30 additionally may control the orbital rotation of the detector columns 22 around the edges of the gantry bore, such that the detector columns 22 are at a new angle to the patient 24 than previously. The detector controller 30 may also optionally control movement of the collimators 26, such as independently of the detector columns 22. It should be noted that one or more the detector columns 22 and/or the collimators 26 may move during imaging operation, move prior to, but remain stationary during imaging operation, or may remain in a fixed positioned or orientation. In various embodiments, the detector controller 30 may be a single unit controlling movement of both the detector columns 22 and the collimators 26, may be separate units, or may be a single unit controlling only operation of the detector columns 22 or may be a single unit controlling only operation of the collimators 26.

The imaging system 20 also includes an image reconstruction module 34 configured to generate images from acquired image information 36 received from the detector columns 22. For example, the image reconstruction module 34 may operate using NM image reconstruction techniques to generate SPECT images of the patient 24, which may include an object of interest, such as the heart 28 of the patient. The image reconstruction techniques may be determined based on the installation status of detector column 22 acquiring the image information 36 and sending to image reconstruction module 34 and/or processor 32.

Variations and modifications to the various embodiments are contemplated. For example, in a multi-headed system, namely a system having two or more detector columns 22, each detector column 22 may be formed from different materials and have different collimators 26. Accordingly, in at least one embodiment, one detector combination may be configured to obtain information for an entire field of view (FOV), such as the entire spine, while another detector combination is configured to focus on a smaller region of interest (ROI) to provide higher quality information (e.g., more accurate photon counting). Additionally, information acquired by one detector combination may be used to adjust the position, orientation, etc. of at least one other detector combination during imaging.

The image reconstruction module 34 may be implemented in connection with or on a detector controller 30 and/or processor 32 that is coupled to the imaging system 20. Optionally, the image reconstruction module 34 may be implemented as a module or device that is coupled to or installed in the detector controller 30 and/or processor 32. Each processing module may be a separate hardware module or software module, or combined together into one chip or module in various embodiments.

The image information 36 received by the processor 32 and/or image reconstruction module 34 may be stored for a short term (e.g., during processing) or for a long term (e.g., for later offline retrieval) in a memory 38. The memory 38 may be any type of data storage device, which may also store databases of information. The memory 38 may be separate from or form part of the processor 32. A user input 39, which may include a user interface selection device, such as a computer mouse, trackball and/or keyboard is also provided to receive a user input. The user input may direct the processor 32 to send a detector control signal to the detector controller 30 for alteration of the detector column 22 arrangement in the gantry bore. Optionally, the user input 39 may be considered by the processor 32 as a suggestion and the processor 32 may choose to not execute the suggestion based on criteria.

Thus, during operation, the output from the detector columns 22, which may include the image information 36, such as projection data from a plurality of detector/gantry angles is transmitted to the processor 32 and the image reconstruction module 34 for reconstruction and formation of one or more images. The reconstructed images and other user output can be transmitted to a display 40 such as a computer monitor or printer output. The reconstructed images and other user output can also be transmitted to a remote computing device via network 42.

Different combinations and variations of detector columns 22 and/or collimators 26 will now be described. It should be noted that the various embodiments are not limited to a particular detector, collimator, or detector combination, but may include any imaging system having a plurality of different types of detector columns 22 and/or collimators 26, for example, having at least two detector columns 22 of a different type or design. Additionally, the number of detector columns 22 and the arrangement thereof may be varied as desired or needed, for example, based on the type of imaging to be performed or the type of image information to be acquired. Accordingly, various embodiments include the imaging system 20 having a plurality of detector columns 22, wherein at least two of the detector columns 22 are different and are configured to perform imaging of the patient 24 (or other object).

For example, in one embodiment, illustrated in FIG. 2, a configuration is provided having one detector column 22a formed from one material and the remaining detector columns 22b-22l formed from a different material. In the illustrated embodiment, the detector column 22a is formed from a NaI material and the remaining detector columns 22b-22l are formed from a CZT material. Accordingly, in this configuration, a single NaI detector column 22a and a plurality of CZT detector columns 22b-22l are provided. The detector columns 22a-22l may be sized and shaped the same or differently. For example, in the embodiment illustrated in FIG. 2, the NaI detector column 22a is larger than each of the CZT detector columns 22b-22l, such that the NaI detector column 22a can image the entire patient 24 and the CZT detector columns 22b-22l are configured to focus on a portion of the patient 24, such as the heart 28. In this embodiment, one or more of the CZT detector columns 22b-22l may be positioned and oriented at different angles or tilted differently to provide focused imaging. However, one or more of the CZT detector columns 22b-22l may be angled or tilted the same. In the embodiment of FIG. 2, the CZT detector columns 22b-22l are angled such that together the CZT detector columns 22b-22l focus on the overall body of the patient 24, instead of on a particular ROI, such as the heart 28. Thus, one or more detector columns 22 may be arranged and configured to cover an entire FOV of an imaged, while one or more other detectors are arranged and configured to cover a focused FOV within the object.

It should be noted that as used herein, a set of detectors is generally referred to as the detector columns 22 and a set of collimators is generally referred to as the collimators 26. Moreover, the use of letter designations after the numeral designation for the detector columns 22 and collimators 26 are used for ease of illustration and do not necessarily represent the same detector columns 22 or collimators 26 in the various embodiments or figures. Thus, the letter designation represents the relative positioning of the detector columns 22 or collimators 26 and not necessarily the type or kind of detector. Additionally, the size and shape of the detector columns 22 may be varied as desired or needed.

In FIG. 2, the collimators 26a-26l may be the same or may be different. For example, the collimator 26a may be of a first type, such as a parallel hole collimator, while the collimators 26b-26l may have different types (e.g., converging, diverging or pinhole) based on a desired or required sensitivity or resolution, as well as the position and orientation of the detector column 22 on which the collimator 26 is coupled. Thus, the collimators 26 may be of any type.

Figure 3:
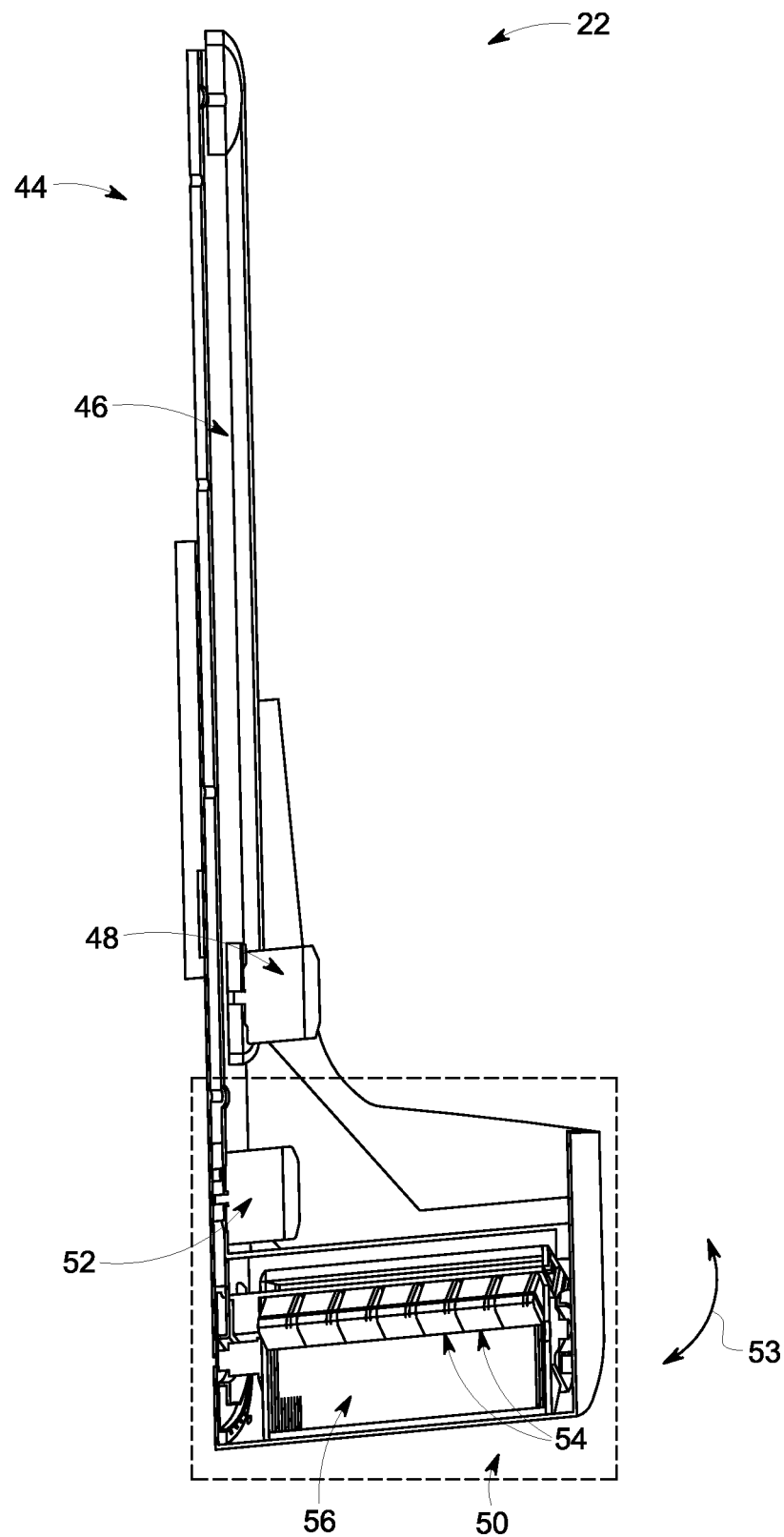
FIG. 3 is a detailed view of a detector column design.

FIG. 3 shows a more detailed implementation of detector column 22 in accordance with an embodiment. Column arm 44 attaches to a gantry and provides support for and includes a radial motion rail 46, radial motion motor 48, and detector head 50. The radial motion motor 48 controls the movement of the detector head 50 by extending or retracting the detector head 50 along the radial motion rail 46. This provides customizability and flexibility to the imaging system. The detector column can include telescopic covers that allow it to extend and contract as it moves radially in and out.

The detector head 50 includes a sweep motor 52, detector elements 54, and collimator 56. The detector elements 54 can be CZT modules or other detector element modules discussed throughout for detecting imaging data. Sweep motor 52 controls the rotation angle of the detector head 50 in relation to the arm 44. The sweep pivoting axis 53 shows the rotation angle axis of the detector head 50. The detector controller 30 can provide instruction and control to either or both of the radial motion motor 48 and sweep motor 52. Thus, each detector column 22 is independently controllable in the radial location as well as the angle of tilt of the detector head 50. The radial motion motor 48 and sweep motor 52 can be two separate motors as shown in the embodiment of FIG. 3. Alternatively, the functionality of the two motors may be provided by one motor.

Figure 4A:
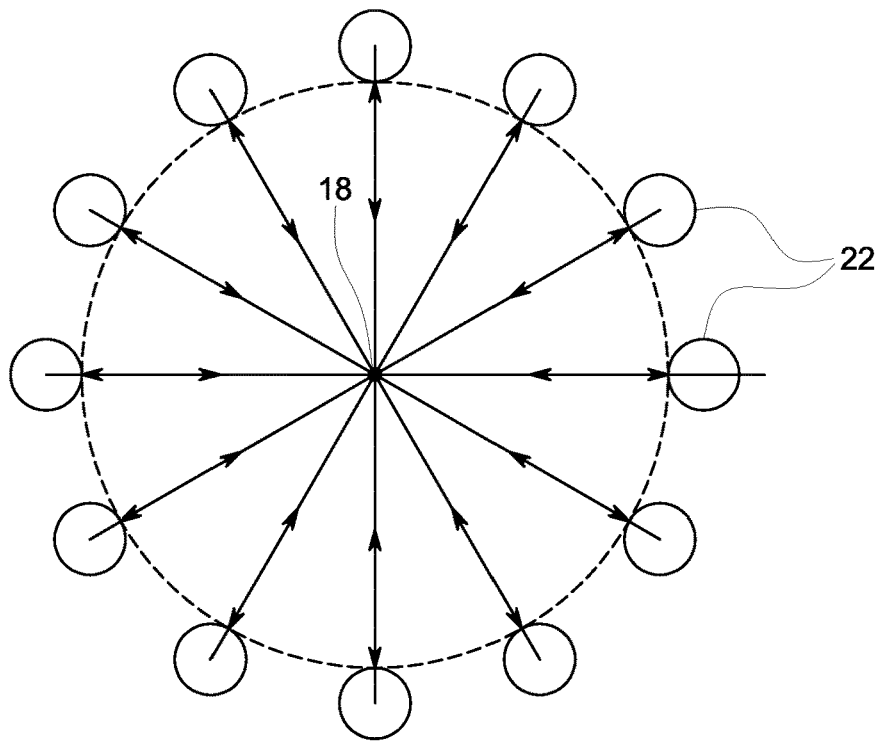
FIG. 4A is a diagram illustrating a radial construction and approach to image detection.

FIG. 4A shows a radial construction of an imaging system where twelve detector columns 22 are placed at a consistent angle, thirty degrees in this example, from each other along the inside of a gantry bore. Thus, the detector columns 22 are uniformly distributed in this example. Each detector column 22 is movable along a radial axis. This allows the detector columns 22 to be closer or further from a subject 18 for imaging. The circles in the figure depict the location of the detector head 50 of detector column 22. The detector columns are shown along the dotted line as their outer limit position in this view of one embodiment. The dual head radial arrows depict the in-out direction of motion of the detector columns 22.

Figure 4B:
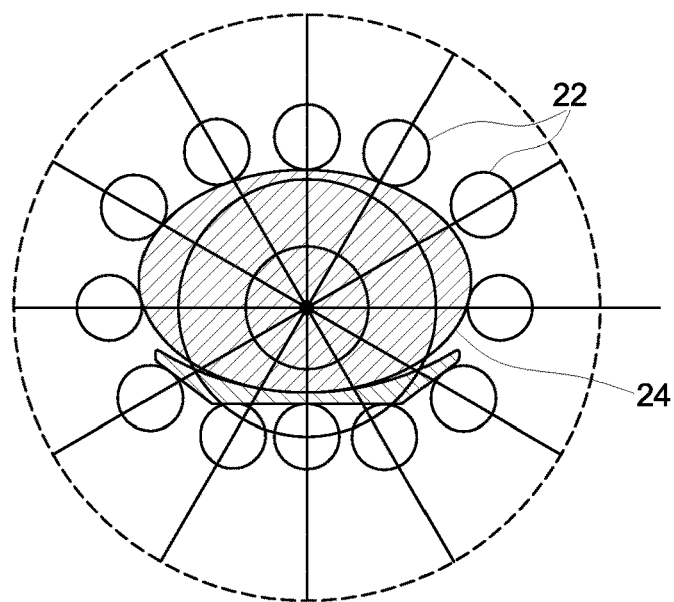
FIG. 4B is a diagram of the detector columns controlled to move at different points of their radial axis to best scan the specific shape of a subject.

FIG. 4B shows a radial construction where twelve detector columns 22 have their heads placed at a consistent angle and have been moved radially inward to be in positions close to a patient 24. As FIG. 4B shows, some of the detector heads are further towards the center of their radial axis than others. This allows for high-quality imaging results with varied-sized objects.

Figure 5:
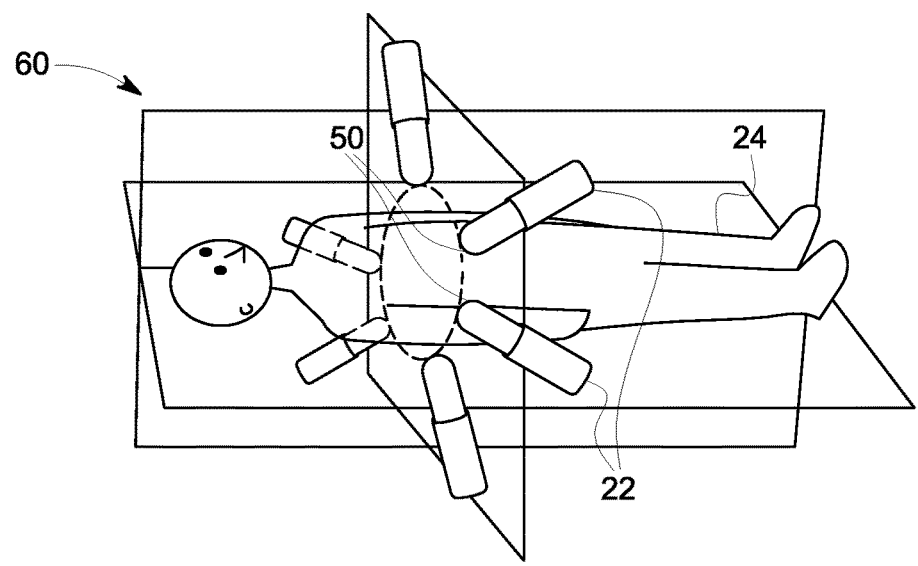
FIG. 5 is a patient centric view of an exemplary medical imaging system.

FIG. 5 shows a NM medical imaging system 60 scanning the mid-section of a patient 24 where the detector columns 22 including detector heads 50 are only partially populated, according to one embodiment. Compared to a fully populated system, such as FIG. 4A and FIG. 4B, a partially populated system includes the installation of a partial amount of detector columns 22 that an imaging system is configured to support. FIG. 5 also demonstrates the planes of scanning including the sagittal plane, coronal plane, and transverse plane. Based on the specific ROI or type of image scan selected, imaging of a patient may only need to be focused in areas of these planes. Some embodiments herein are directed towards tailoring partially populated imaging systems, such as NM imaging system 60 for maximal image quality and lowest scan time given the situation and installation information constraints.

Figure 6:
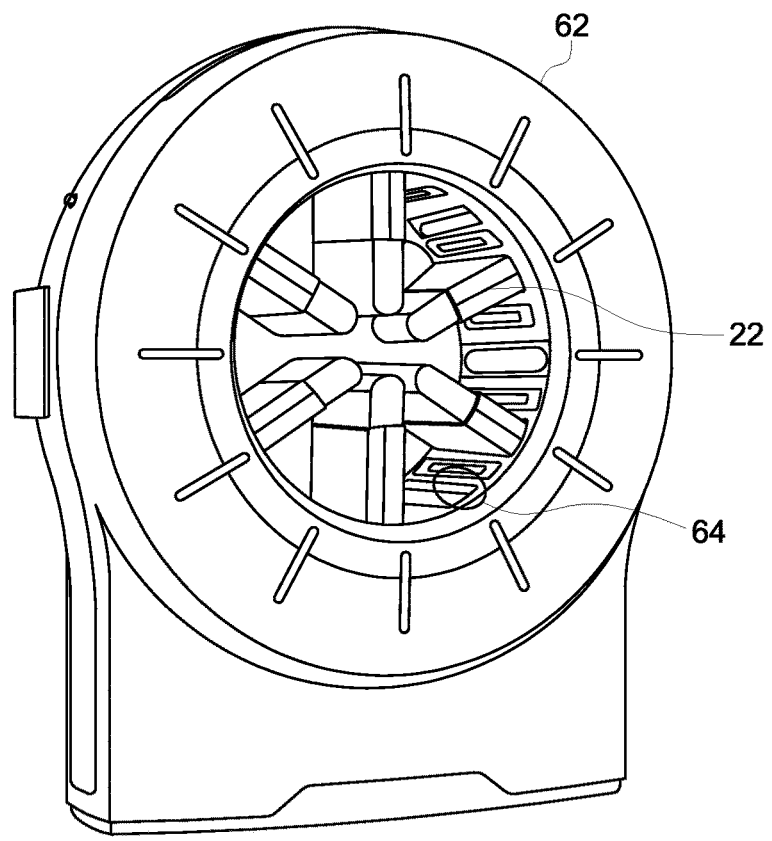
FIG. 6 is a perspective view of a gantry design with detector columns placed in a partially populated configuration.

FIG. 6 shows a gantry 62 that can support twelve detector columns 22. The gantry 62 can contain all of the features of the FIG. 2 system in one embodiment. Only six detector columns 22 have been installed in gantry 62. This could be for lower cost of the system, easier maintenance, or other reasons, for example. Thus, the system of FIG. 6 is a partially populated NM imaging system. It is partially populated because the installation information for the system indicates that the system can support twelve detector columns 22, but only six detector columns 22 are installed. The locations where a detector column can be installed or attached can be called receiver locations 64 in some embodiments. The detector columns 22 in FIG. 6 are shown in a radially extended position. The detector columns 22 of this embodiment can be detached by a non-technical operator. They can be detached from one of the twelve receiver locations 64 and snapped, screwed, clamped, or otherwise attached, to one of the open receiver locations 64 around the gantry 62. Thus, detector columns 22 are detachable and attachable to create further system configurations. This system, in some embodiments, can be considered a modular system. A non-technical operator can be one who has not had specialized or advanced training on the installation and adjustment of the imaging system. A technical operator could be a field engineer, for example.

Installation information can be dynamically updated by processor 32 or detector controller 30 based on information from installation verification elements in receiver locations 64, and stored in memory 38 in one embodiment. Installation verification elements can be any sort of switch, button, sensor, or other device that detects the presence of hardware installed or not installed in the system. Installation verification elements of receiver locations 64 are one way that the system can detect and update installation information. Installation information in one embodiment relates to the detector column arm 44 being physically attached to gantry 62. Further, installation information in another embodiment detects both physical attachment plus a fully functioning arm. In this embodiment, if any of the radial motion motor 48, sweep motor 52, and/or detector elements 54 are inoperable, even though the detector column 22 is attached to the gantry 62, the installation information could indicate the detector column as uninstalled and/or inoperable. Installation information can also indicate the population of specific detector elements 54, as further discussed below.

Installation information is also called configuration information in some embodiments. This is because installation information gives information related to the current hardware configuration in the imaging system, and can be dynamically updated. Thus, installation information, sometimes called configuration information, is not just the initial setup information of the system when delivered to a customer, but is information dynamically updated based on many hardware factors throughout the lifetime of the system.

Figure 7A:
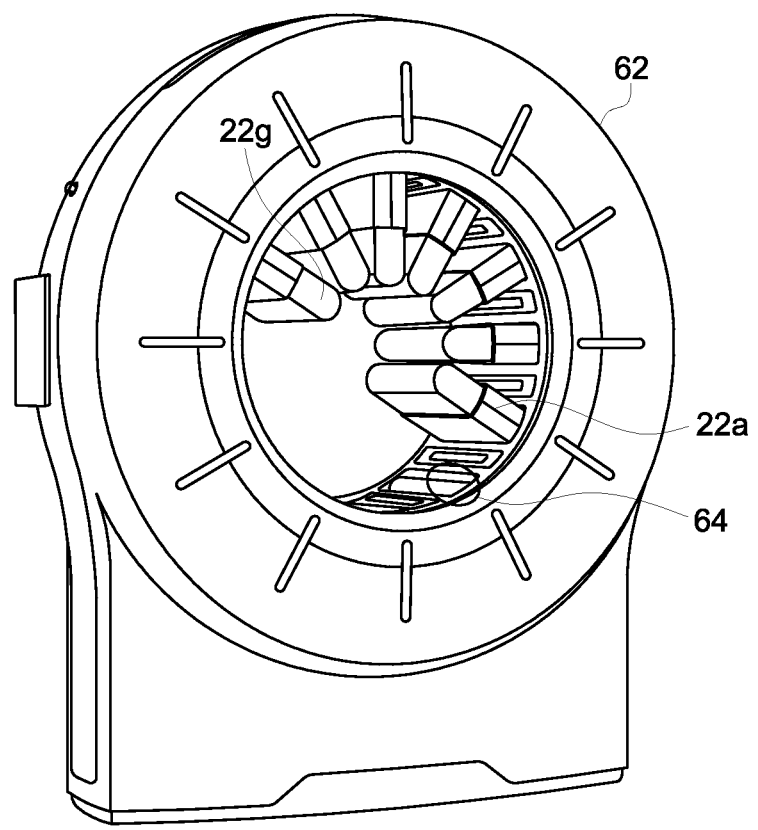
FIG. 7A is a perspective view of a gantry design with detector columns aligned for a supine positioned subject.

FIG. 7A shows a gantry 62 that can support the installation and operation of twelve detector columns 22. Only seven detector columns 22 have been installed in gantry 62. This is an example of a partially populated imaging system. The detector columns 22 in FIG. 7A are shown in a radially extended manner, but not as radially extended as shown in FIG. 6. This configuration may be best for a supine patient where the heart, as an example of a ROI, is near the top and side of the gantry. The detector controller 30 can identify from the installation information that there are seven installed detector columns 22 and in which receiver locations 64 they reside around the bore of gantry 62. Then the detector controller 30 rotates the detector columns 22 around the bore to the ideal position for the particular region of interested based on user input 39 or information of the test and patient from other sources, such as memory 38 or network 42. This ideal position can also be called the position location essential for imaging information. Thus, moving the detector columns 22 and detector heads 50 into the best position for capturing essential imaging information for each type of procedure is important and is done by the embodiments.

Figure 7B:
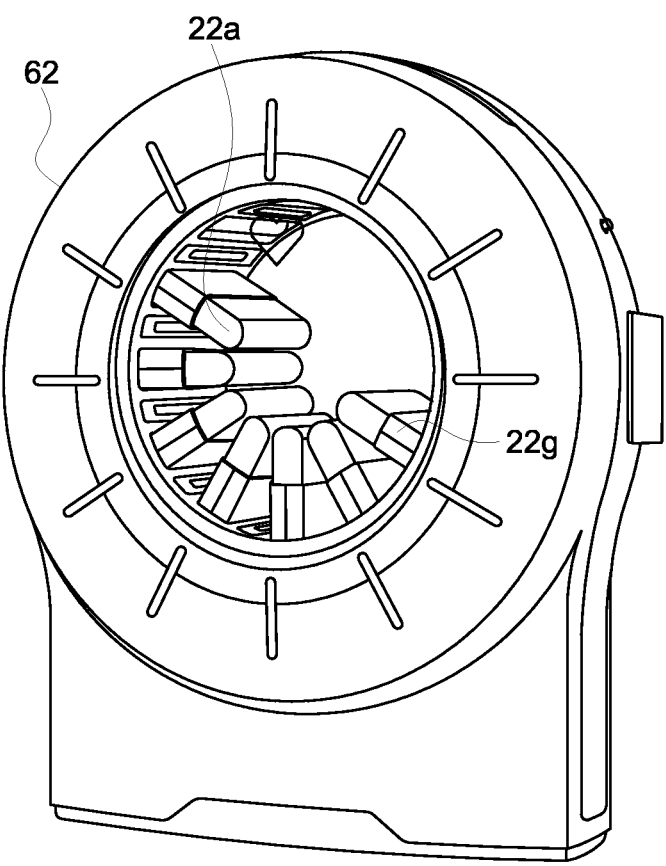
FIG. 7B is a perspective view of a gantry design with detector columns aligned for a prone positioned subject.

FIG. 7B shows a gantry 62 where the seven detector columns 22 have been rotated by machinery in an orbital manner inside the gantry 62 that is controlled by the detector controller 30 to move the detector columns 22 into positions with new radial axes to a patient. The detector columns can be rotated rotate three-hundred sixty degrees around a subject to be imaged, which is patient 24 in this example. As can be seen from comparing FIG. 7A to FIG. 7B, detector column 22a has been rotated from an axial position below a patient 24 to an axial position above the patient 24. Detector column 22g, consequently, has moved from above to below the patient in this example. The example in FIG. 7B may be best for prone patients where the heart, as an example of a ROI, is near the bottom and side of the gantry.

Figure 8:
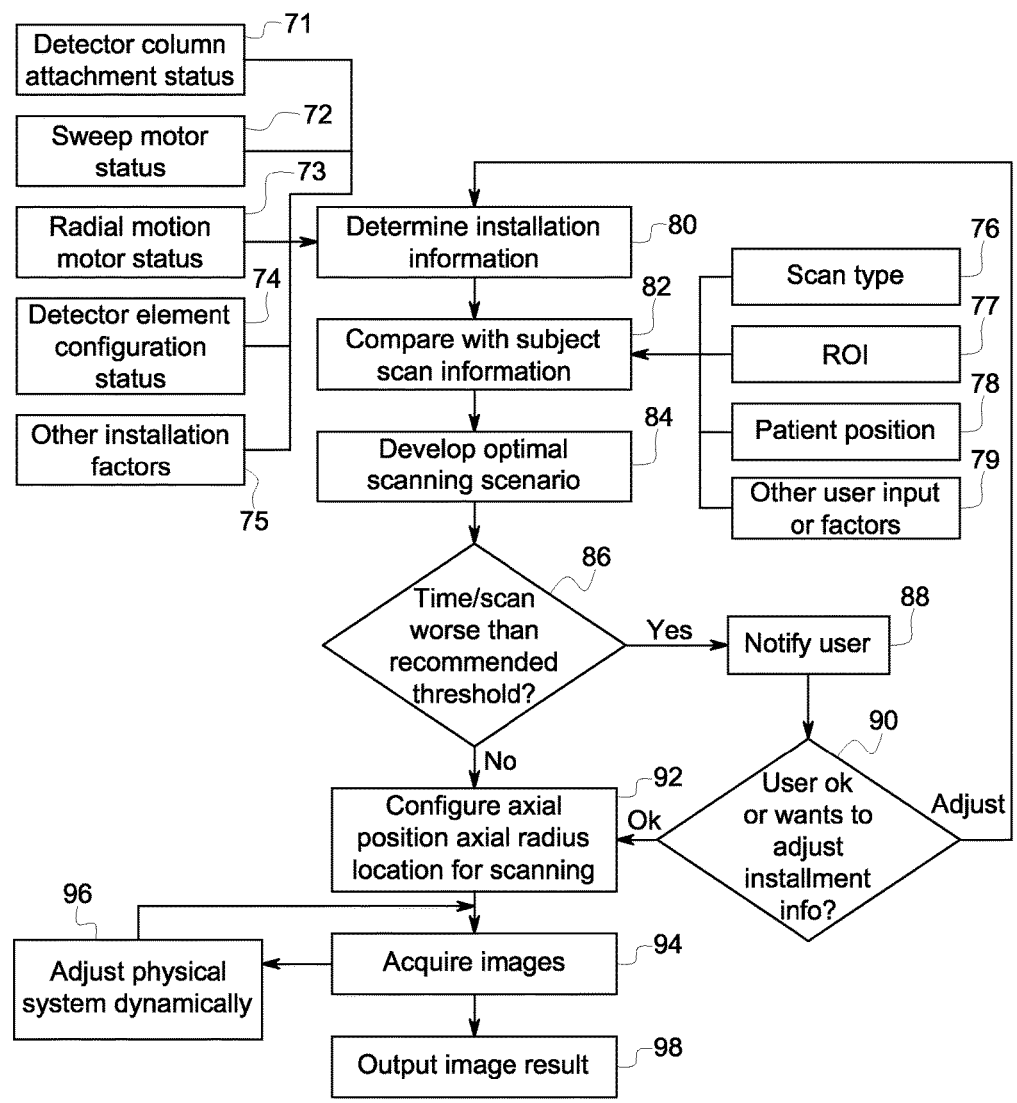
FIG. 8 is a flowchart of a method for controlling detector columns.

FIG. 8 is a flowchart depicting a method of operation with respect to one embodiment. The steps as shown do not necessarily have to flow in the order as listed, but are shown in this order just as an example.

In step 80, the system determines installation information. This helps determine what operations and features are available in the system. Installation information, in some embodiments, can included detector column attachment status 71 which indicates in which receiver locations 64 detector columns 22 are installed and in which receiver locations 64 detector columns 22 are not installed. This can tell the system both how far each detector unit can be extended radially as well as how much orbital movement of the detector units will need to occur during operation. Installation information can further include sweep motor status 72. This status can indicate whether each detector column 22 has a sweep motor 52 for head rotation capability, whether the sweep motor 52 is operable, and its range of motion (in circumstances when some detector heads 50 are configured to rotate further than others), or not responding. Installation information can further include radial motion motor status 73. This status can indicate whether each detector column 22 has a radial motion motor 48, its radial motion distance, radial location status, and whether or not the motor is currently operable. Installation information can further include detector element configuration status 74. This status can indicate the specific locations where detector elements 54 are installed and specific locations where detector elements 54 could be installed but are not installed. See FIGS. 16-17 for example. This status can also indicate what materials are being used to detect the imaging data. Each detector column or detector element could have different scintillator or semi-conductor materials installed. This detector element configuration status 74 can also indicate what collimator 56 structure is used in the detector head. As mentioned above, different collimators 56 can be utilized in different detector heads 50. Installation information can further include other installation factors 75, including gantry rotation ability. This is an indication of how many degrees of rotation (or how many 'steps') the gantry can rotate detector columns around the orbit of the gantry. Installation information can further include other installation factors 75 such as the room the imaging system is set up in, factors input by a user, safety information, and other types of information about the installation of the system overall, not just the installation status of the components in the imaging system. For example, many SPECT systems are placed in SPECT/CT (computed tomography) combined system, and the system may also acquire information related to what CT setup is installed.

In step 82, the system compares the installation information with what a specific imaging scan will be and subject information. The imaging scan type information 76 (such as CT, SPECT, PET, MRI, or can be related to the specific radiopharmaceutical being used or the type of medical examination performed) can be considered. The region of interest information 77 (such as cardiac, brain, thyroid) can be considered. The patient position information 78 on the pallet or bed can be considered. The subject size, age, gender, weight, and other medical characteristics (patient body-type information or patient medical information or subject specific information) can impact the process relating to other user input factors 79. The imaging scan is generally a NM imaging scan based on acquiring SPECT data, but the system could be used in other scanning arrangements for other types of imaging information.

In step 84, the imaging system 20 develops an optimal scanning scenario based on the installation information compared with the subject scan information. For example, if the scan is a cardiac scan and the subject patient is small, a selected scenario would set the radial extension of the arms to high and the arms will be recommended to move orbitally towards the sides of the gantry closest to the heart. If the angle of the subject is difficult, the scenario may include rotating some of the detector heads 50 to be more accurately aligned towards the subject.

In step 86, the system makes a decision whether the scanning scenario can be performed within a threshold time. This can also be called a total imaging operation time prediction. This determination considers how long it will take the system to do the full requested imaging based on the imaging time plus system rearrangement time when it is being reconfigured to get additional scanning data. The threshold can be based on an 'acceptable' time set by a user, a subject patient preferred time, a normalized time compared to most scans of the type being done, and/or related to a threshold of safety. The total imaging operation time prediction also considers how long it may take to adjust the patient and how long it takes to adjust the detector columns, detector heads, and/or detector elements. If the time to complete the optimal scanning scenario is higher than a threshold, the system goes to step 88, otherwise continuing on to step 86.

In step 88, a user is notified that the current installation setup of the system may not be able to complete the requested scan in a threshold time. A list of options may also be presented to the user relating to steps the user can take to mitigate any issues or override the issue.

In step 90, the user decides whether to alter the installation arrangement/setting of the system or not. The user can input a response back to the system of their intention. The user can adjust the system manually, in some respects, and automatically through computer control in other respect. If a user adjusts the system, thus altering installation information, the method returns to step 80 to re-evaluate the installation information. If the user is OK with the time threshold being met or exceeded, the system can proceed to step 92.

In step 92, the system performs the physical modifications recommended in the optimal scanning scenario. This can include configuring the detector column axial position around the gantry orbit, the axial radius location for scanning (how far or close to patient along the axial radius), detector head angle as controlled by the sweep motor, and other physical adjustments discussed throughout.

In step 94, the subject is in the system and the images are acquired. If multiple physical positions of the detector columns 22, detector heads 50, and/or detector elements 54 are needed, the system adjusts them during the imaging operation at step 96. This is an example of dynamically adjusting of the physical system.

In step 98, the final requested image data is output. A reconstruction algorithm may be applied after the image data acquisition or proactively during the image data acquisition. The output can be to a display, network connected computing device, a printer, picture archive and communication system (PACS) or other output location.

Because the imaging system of at least one embodiment can start with limited installation equipment, the system can perform lower-cost imaging, while also providing upgradability. For example, if a hospital has a small budget and only will perform cardiac scans, they can purchase a system with detector columns setup best for cardiac and not including additional detector columns that can add additional cost. The hospital can still do other types of scans, but will have to wait longer for the system to re-adjust to different image scan scenarios to handle the different scan type. This can add time and sometimes provide a lower quality image than a fully populated or otherwise customized system. The hospital can upgrade and purchase more detector columns, or detector columns with the optional detector head sweep feature, or detector columns with the optional detector radius extension feature, or detector columns with multiple types of image acquisition materials and install them into the system for improved performance. This also applies to detector elements. Detector elements are a driver of cost as well. So a hospital, for example, could purchase one with lower detector element count (with longer scan time, seen for example in FIG. 16B) and upgrade later.

Figure 9:
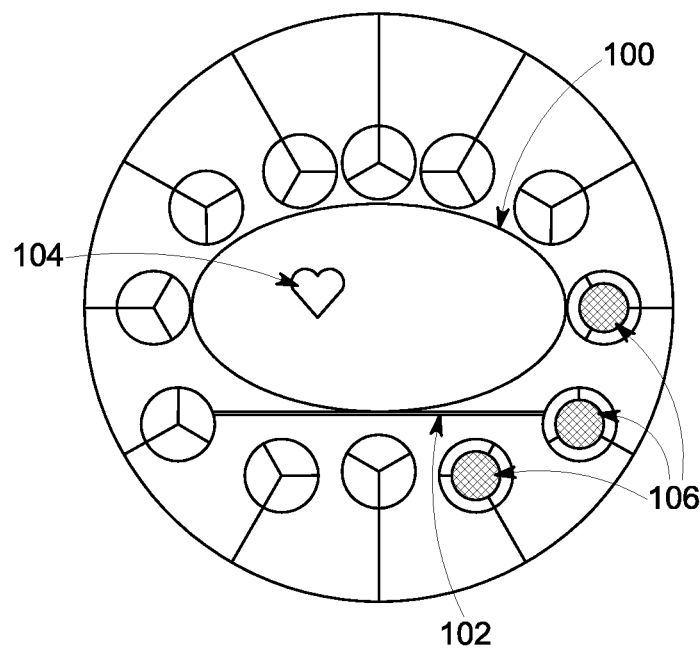
FIG. 9 is a radial construction view of a gantry design with detector columns aligned for a cardiac application.

FIG. 9 shows the front view of an imaging system specifically set to target a cardiac image. A patient 100 lies on a bed 102, which could also be similar to the pallet 14 and bed mechanism 16 of FIG. 1, with their heart 104 on the left side of the system in this view. For this cardiac application, distant locations 106 can either be unpopulated (empty) of any detector columns or they can be set to not receive images (such as, to save electricity). In this case, the unused detector columns may be retracted and not advance towards the patient. This can also be beneficial when one of the detector columns in the system has a broken aspect, such as one of its motors, wires, arm, or detector elements. They system can orbitally move that broken detector column into a distant location 106 to not be used in the current scan. A notification can be sent to the user or operator regarding the issue, the user or operator can be at a local display or remote facility. The system, in this embodiment, does not need to use any detector columns in distant locations 106 because they are too far from the subject, for example, and the distance reduces resolution of the image and adds attenuation from the gamma ray source, patient heart 104 in this example. Thus, the image contribution of any detector columns in distant locations 106 is negligible.

Figure 10:
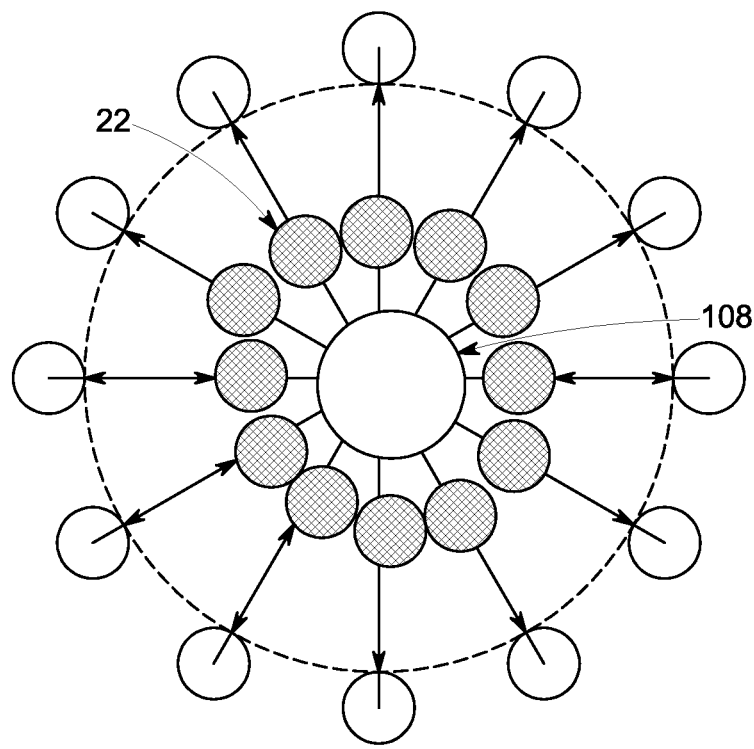
FIG. 10 is a radial construction view of a gantry design with detector columns aligned for a brain or pediatric application.

FIG. 10 shows the front view of an imaging system specifically set to target a small subject such as a brain, a limb, or pediatric image. In this imaging operation, the patient area 108 is smaller than a full body. The detector columns 22 have their heads extend radially from their starting position on the outer limits of the gantry towards the patient 108 to get the best image resolution by being closer, in this example. This example shows a case where a fully populated, all twelve detector column receiver locations in the gantry are filled with detector columns, system is not necessarily ideal, because the arms collide as they try to get the closest distance from the patient area 108.

Figure 11:
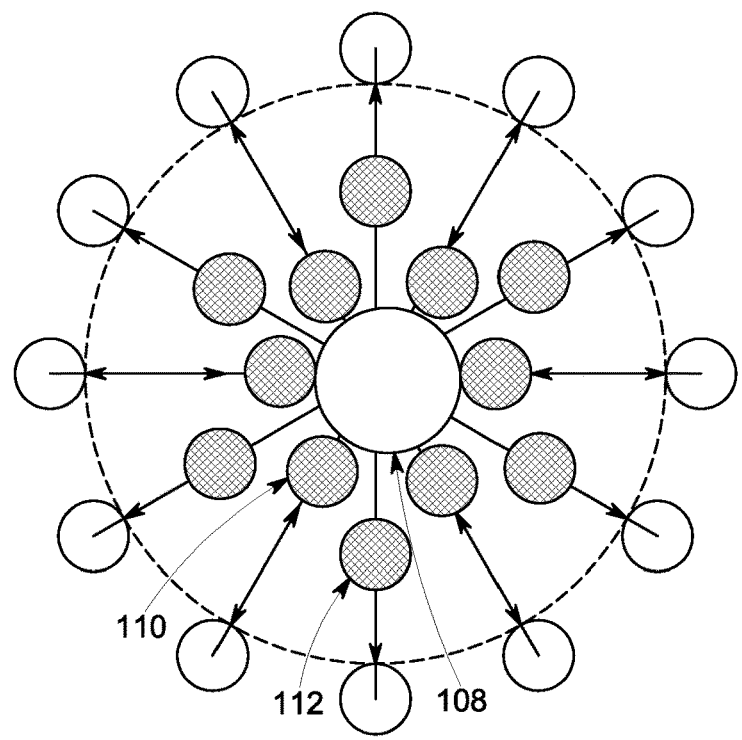
FIG. 11 is radial construction view of a gantry design with detector columns aligned differentially for a brain or pediatric application.

FIG. 11 shows another front view of an imaging system specifically set to target a brain or pediatric image. This is a similar situation to FIG. 10, but the system, following the flowchart steps of FIG. 8 or FIG. 13, determines the installation information (in this case, as an example, a fully populated system with twelve detector columns where the radial motion motors are all in operation), takes in the subject scan information (either the fact that the scan type is a head—small in size, or the subject type is a child—small in size), and develops an optimal scanning scenario. This case includes some fully extended detector columns 110, in this case every other, with some not-fully extended detector columns 112. In FIG. 10, an implementation with fully extended detector columns 110 was not possible because of detector column collision. By not uniformly extending the detector columns, such an implementation is possible in the scenario of FIG. 11.

Figure 12:
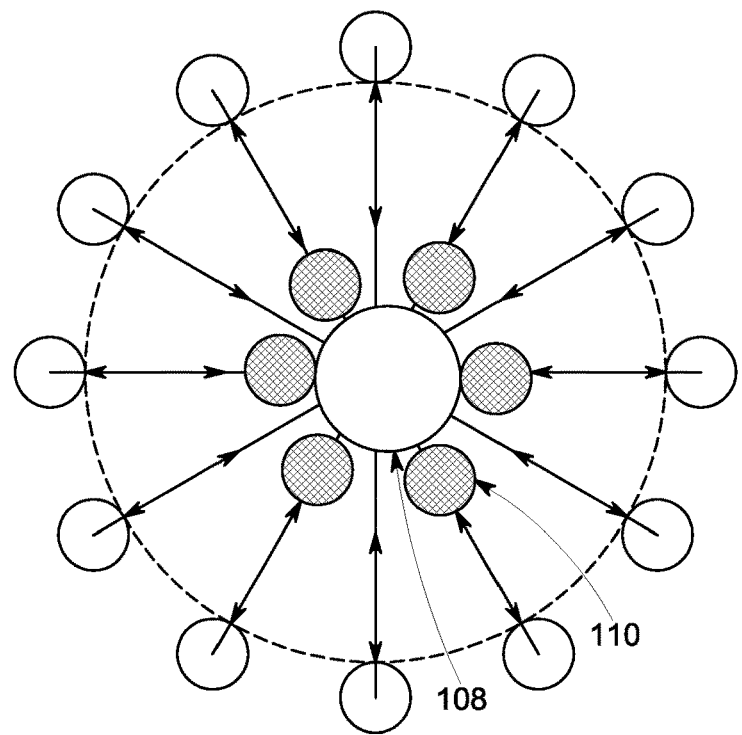
FIG. 12 is radial construction view of a gantry design with partially populated detector columns for a brain or pediatric application.

FIG. 12 shows another front view of an imaging system specifically set to target a brain or pediatric image. In this system, similar to FIG. 6, only half of the possible receiver locations for detector column installation have detector columns installed. A user, either technically savvy or not technically savvy depending on specific hardware implementation, could have removed the detector columns that were not needed from the system. A customer could order from the supplier an imaging system with only some of the detector columns installed, for cost reasons for example. Or, a customer could purchase a fully populated system of FIG. 10 or FIG. 11, and some of the detachable detector columns can be removed at a later time. This creates flexibility and upgradability for users and owners of the system. If a particular imaging system user simply focuses on brain imaging in their imaging operations, they may never need the extra detector columns, with related cost and maintenance, of a fully populated system of FIG. 10 or FIG. 11.

Figure 13:
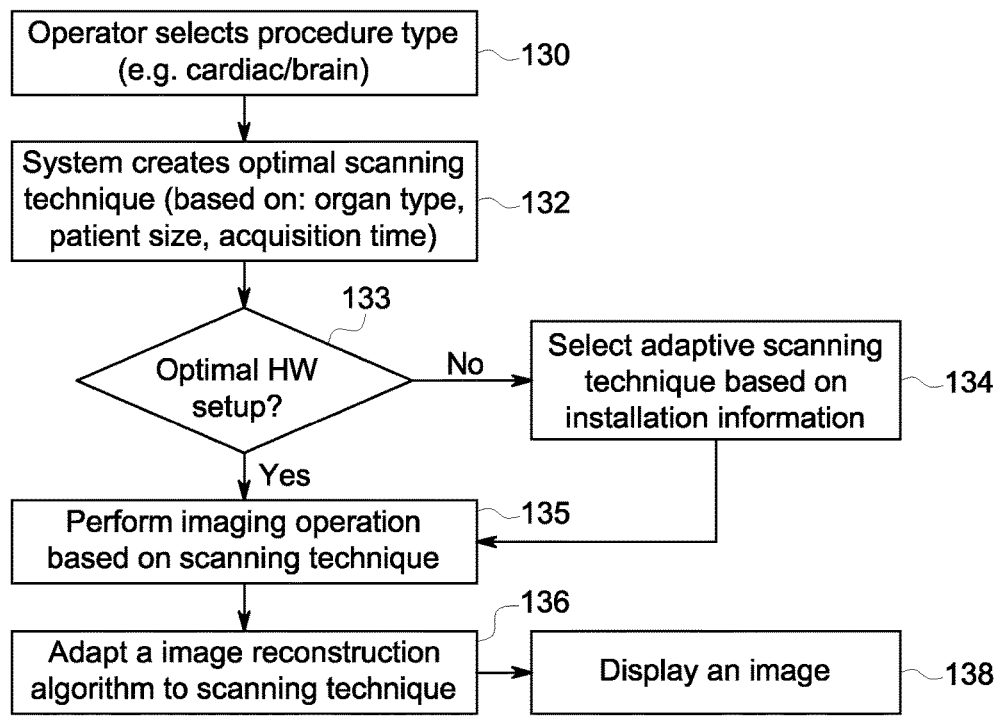
FIG. 13 is a flowchart of a method for controlling detector columns in a partially populated configuration.

FIG. 13 shows a flowchart of the operation of the system in an embodiment. In step 130, the system operator gives a user input 39 indicating the procedure type, such as a brain scan, breast scan, cardiac scan, or other object scan.

In step 132, the system creates an optimal scanning technique of how the detector columns 22, detector heads 50, and detector elements 54 should be arranged. This optimal scanning technique can be based on organ type, patient size, desired acquisition time, for example. These can be user input values for each, or system detected values. For example, the patient size could be automatically determined by a quick scan of the environment.

In step 133, the system determines if the hardware installed in the system can perform the optimal scanning technique. This can also be thought of as a determination if the optimal hardware setup is in place for the current situation based on installation information. If the system has all of the hardware installed for an optimal result (meaning the installation information matches the optimal scanning arrangement), the system proceeds to step 135. Otherwise, it proceeds to step 134.

If the system reaches step 134, the system has used the installation information to determine that the optimal scanning technique cannot be performed. This could be, for example, that one detector column is missing so the optimal arrangement cannot be accomplished and the scan time will necessarily be longer. In step 134, the system, using the installation information and/or other factors related to the scan type or scan object, creates a new adaptive scanning technique to meet the situation or retrieves a previously saved adaptive scanning technique from memory that can apply to the current situation. The adaptive scanning technique can add time to the scan, but can be lower cost because the operator or customer does have to pay for a fully populated or fully featured system. Optionally, the adaptive scanning technique may comprise gantry motion or rotation or both in order to bring an operating detector to a location where a missing or inoperative detector should have been.

In step 135, the system performs an imaging operation on the subject. The imaging operation is completed by controlling the hardware elements of the system in a manner fitting the selected scanning technique (either optimal or adaptive). This controlling can include, but is not limited to, extending or retracting detector columns 22, rotating detector heads 50 to different scan angles, or moving detector columns 22 around the gantry orbitally to a new radial angle to the subject (such as the orbital movement of detector columns between FIG. 7A and FIG. 7B).

In step 136, the system adapts a reconstruction algorithm based on an image acquisition scenario and reconstructs the imaging information picked up on the detector elements 54 using imagine reconstruction module 34. The image reconstruction process or algorithm can be adapted to be more compatible with the selected scanning technique. This creates the highest quality image possible given the hardware constraints of the system.

In step 138, the system displays an image output to a user, operator, patient, or other party. This can be on display 40 or at some remote location after the image output has been transmitted over network 42.

Figure 14:
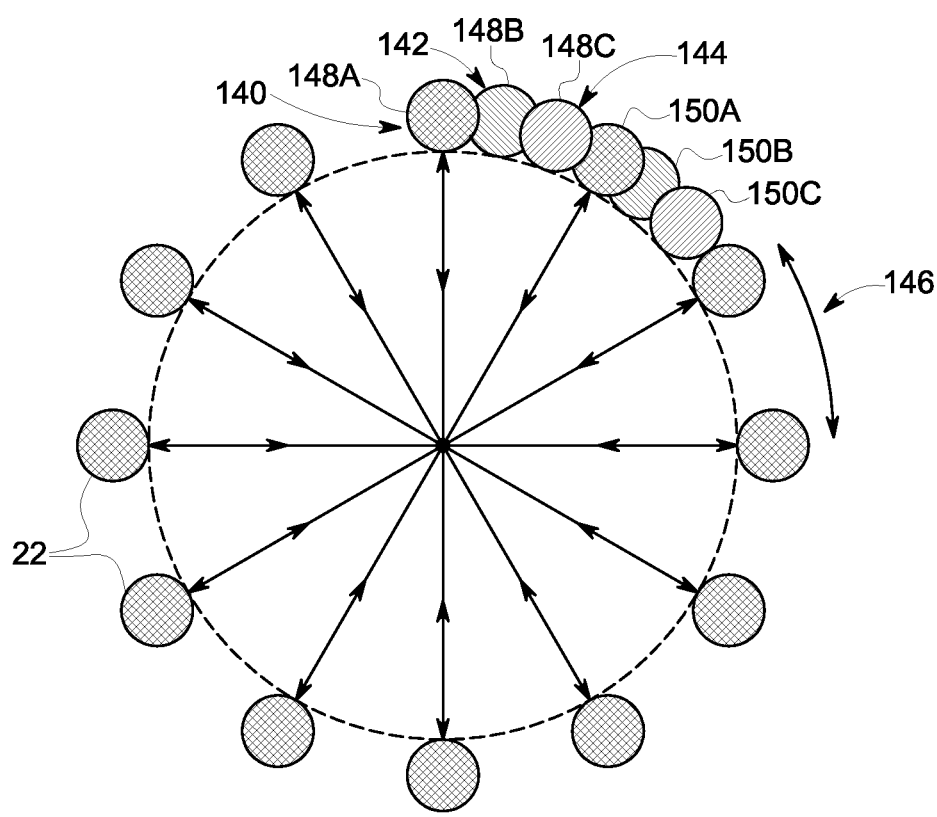
FIG. 14 is a radial construction view of a gantry design with step-enabled detector columns.

FIG. 14 shows the ability of the gantry to rotate the detector columns in an orbital manner. Detector columns 22 are placed at even angles from each other in this fully populated example. The gantry rotation range 146 is a full three-hundred sixty degree rotation in some embodiments, as low as zero degrees in other embodiments, and may be anywhere in between. Again, this is an upgradeable feature and related to installation information. The gantry can be initially installed with hardware only supporting thirty degree rotation, for example. The customer could then purchase an upgrade with a few additional motors or hardware components to be installed to give the gantry one-hundred eighty or three-hundred sixty degree rotation ability. FIG. 14 shows a system with a thirty degree gantry rotation range 146. This allows a twelve detector column system to give coverage every ten degrees. FIG. 14 shows detector column 148A at an initial position 140, step 1 of rotation. Detector columns 148B and 148C are the same physical detector column as 148A, just in new orbital positions 142 and 144, respectively. FIG. 14 further shows detector column 150A rotated to different orbital positions 150B and 150C. Thus, the system can rotate orbitally to move all detector columns to a new radial angle from a subject, or just move specific detector columns to new locations without rotating all of the detector columns in the system. FIG. 14 shows the latter arrangement, when only detector columns 148A and 150A are rotated an all other detector columns 22 remain at the same radial angle with respect to a subject.

Figure 15:
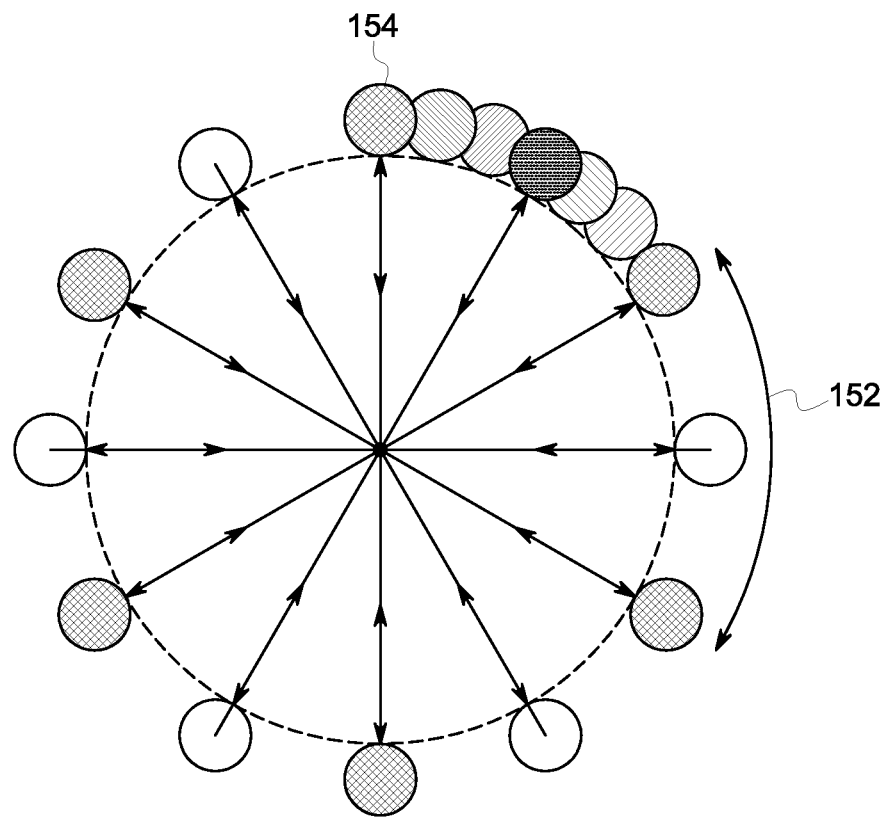
FIG. 15 is a radial construction view of a gantry design with partially populated step-enabled detector columns.

FIG. 15 shows the ability of a partially populated gantry to rotate the detector columns, such as detector column 154, in an orbital manner. In this example, the column detectors only partially populate the gantry locations. Six gantry locations, at sixty degree intervals have detector columns installed, while alternating six locations are vacant. The gantry rotation range 152 is sixty degrees in this example, and a detector column 152 has six 'steps' or locations of scanning, each set at a ten degree offset.

Figure 16A:
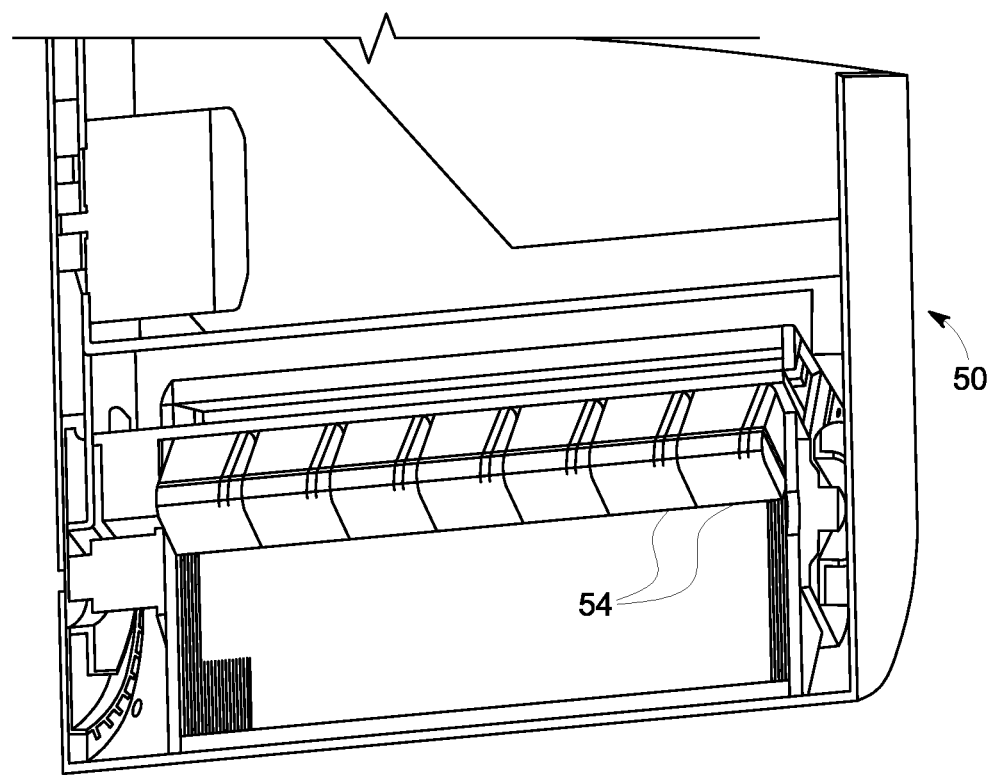
FIG. 16A is a detector column view with fully populated detector elements.

FIG. 16A is a detailed view of a fully populated detector head 50. It shows detector elements 54 that include the detector materials to pick up photons or other imaging indicators in an imaging operation. The detector head 50 of FIG. 16A is considered fully populated because all seven of the locations where detector elements can be installed have installed detector elements 54. Whether a detector element 54 is installed or vacant can be one type of installation information. Also, the type of materials embedded in each detector element 54 can be one type of installation information. The head may have any number of detector element locations; seven is just the example of this particular embodiment.

Figure 16B:
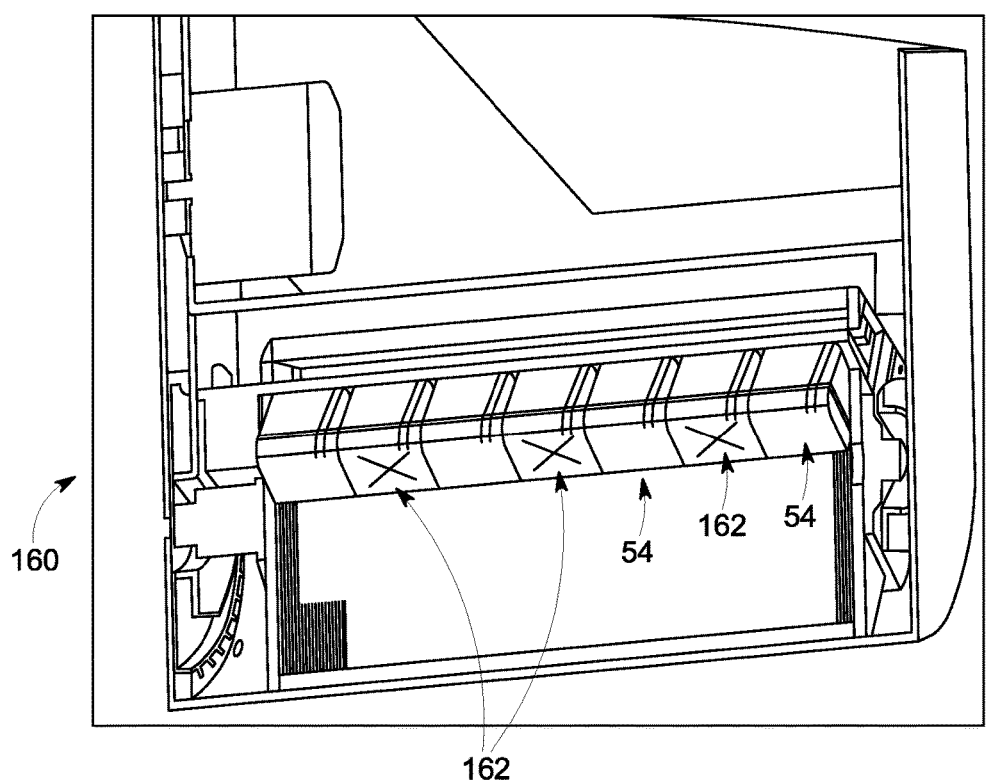
FIG. 16B is a detector column view with partially populated detector elements.

FIG. 16B is a detailed view of a partially populated detector head 160. The detector elements 54 are installed in a staggered fashion, with vacant detector element locations 162. This installment configuration provides for a lower cost detector column 22, because much of the cost of a detector column comes from the detector element 54. The collimator may be sized to the number of populated detector elements. In this case, even locations are vacant, and odd locations are populated.

Figure 16C:
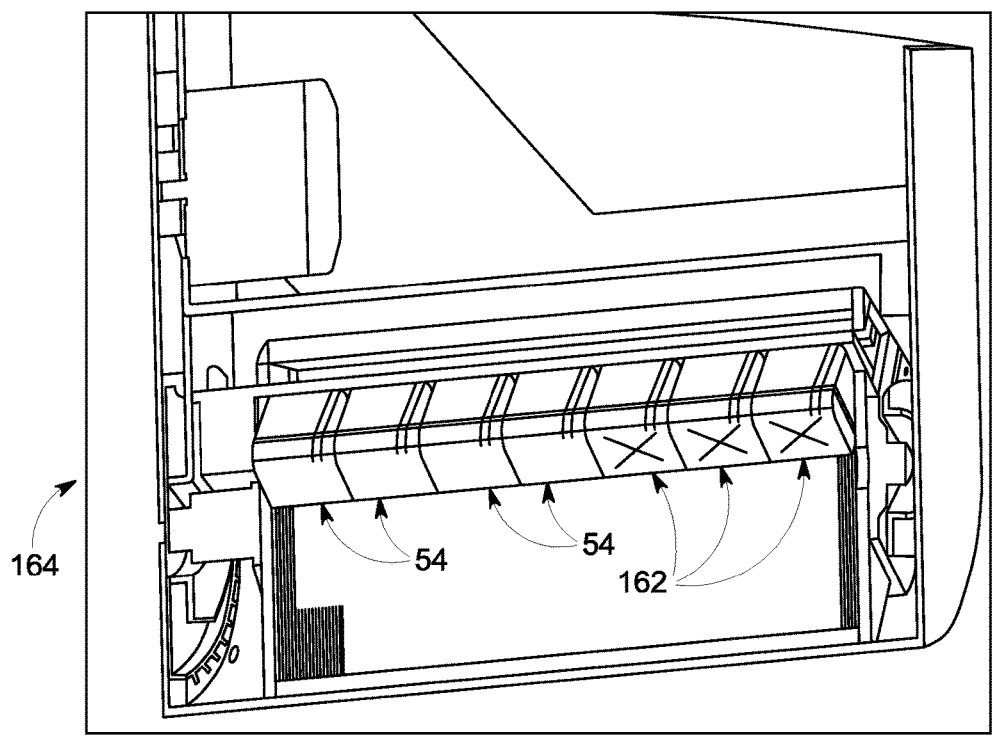
FIG. 16C is a detector column view with partially populated detector elements.

FIG. 16C is a detailed view of a partially populated detector head 164. The detector elements 54 are all installed towards one side of the detector head 164. Vacant detector element locations 162 are towards the other side of the detector head 164. This installation configuration can be good for narrow field of view imaging operations. The narrow field of view installation configuration can be good for small organ scanning, such as having five detector elements 54 installed for brain scans (20 cm coverage), four detector elements 54 installed for heart scans (16 cm coverage), or two detector elements 54 installed for thyroid scans (8 cm coverage). As an example, if a system including only two detector elements 54 per detector column 22 was trying to complete a brain scan, the time to do the brain scan could be much longer or the image result could be much worse. Step 86 of FIG. 8 could determine this and notify the user at step 88. The user could then swap out the current detector columns with others that have five detector elements per detector column. The system would then dynamically update the installation information in step 80. Thus, the system is reconfigurable and customizable to fit user needs and imaging situations. A medical facility, for example, in which the majority of scans are of limited axial extend, such as brain, thyroid, heart, and the like may choose the appropriate population for their system to reduce cost. Axial FOV larger than the width of the populated section of the heads, for example, whole body scanning, may be achieved with axial motion of the patient table.

Figure 17A:
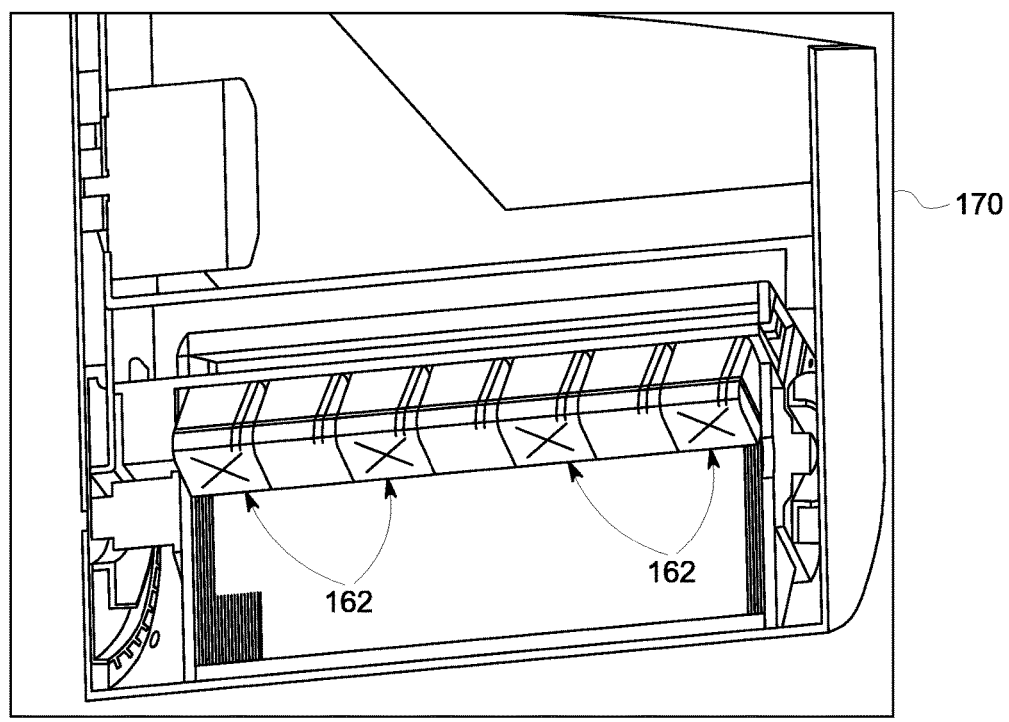
FIG. 17A is a detector column view with only even detector elements populated.
Figure 17B:
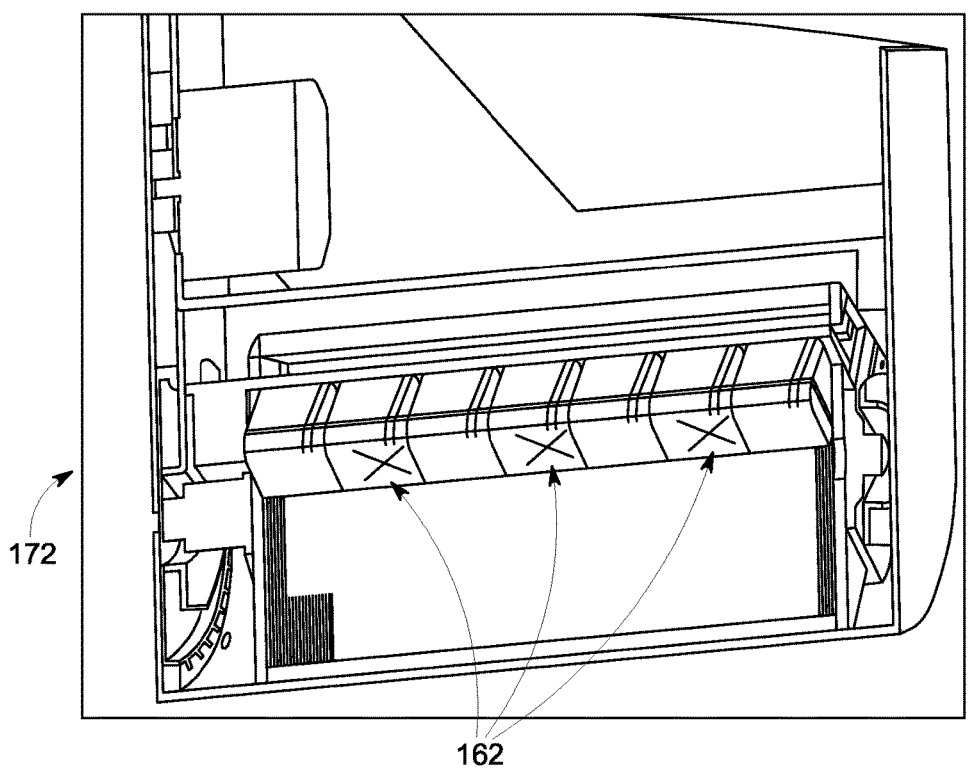
FIG. 17B is a detector column view with only odd detector elements populated.

FIG. 17A and FIG. 17B show detailed views of partially populated detector heads. In a system, such as FIG. 20, where a gantry has fully populated detector columns 22, the odd numbered detector columns could have odd populated detector elements, such as in detector head 170. The even numbered detector columns could have even populated detector elements, such as detector head 172. Thus, the installation information can vary from one detector column to the next detector column.

Optionally, the populated detector elements in the detector columns are arranged in an alternating fashion such that a combination of detector elements in two adjacent detector columns creates a full set. This allows for acquiring a full data set by positioning odd columns in the position where an even column was before, and combining the data acquired from the two columns from at the same position. It should be noted that positions may not be identical, but only proximate to enable successful reconstruction. Optionally, adjacent columns may have at least one common populated element or a common missing element and yet enable successful reconstruction. Generally, "over sampling" as created by common populated element is easily compensated in the reconstruction and reduces the noise in the parts of the scanned body which was over sampled. Under sampling as created by common unpopulated element may also be compensated in the reconstruction, but it may increase the noise in the parts of the scanned body which was under sampled. However, not all parts of the body need to be scanned at the same accuracy, and thus under sampling may be tolerated if aimed at less critical organs.

Figure 18:
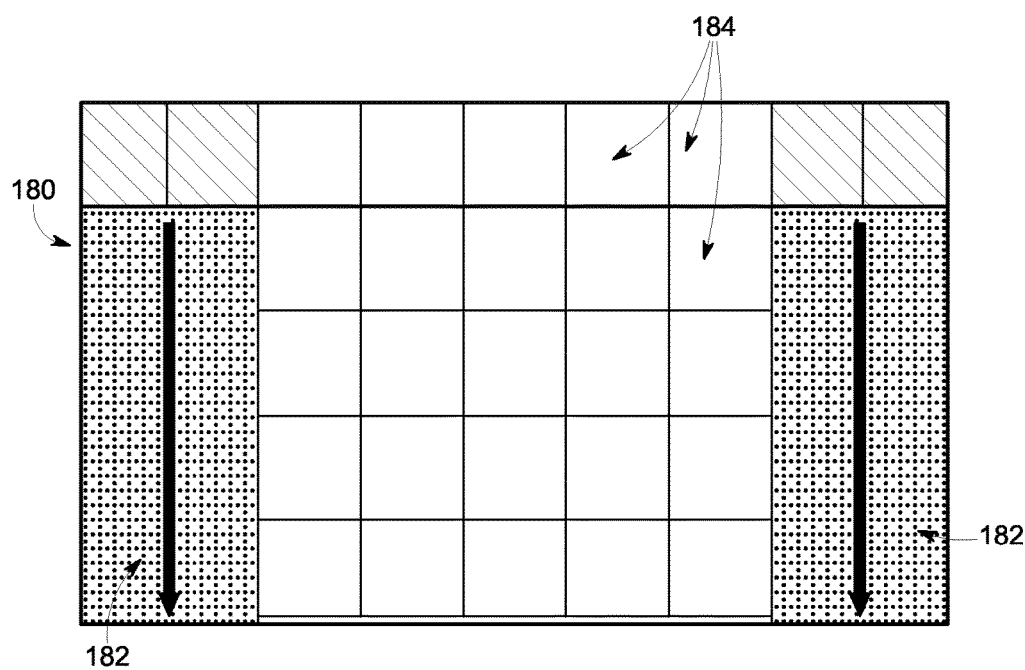
FIG. 18 is a detector element view where the outside detector elements are movable or slide-type.

FIG. 18 shows a detailed view of a detector head design of another embodiment. The detector elements of detector head 180 are arranged in a grid. When targeting a specific organ or subject, the direct detector elements are most important for image quality, and the detector elements further to the side are only necessary for peripheral information. Thus, to save cost, detector heads can be configured as shown. The middle region with fixed detector elements 184 give five times better sensitivity than the detector elements 182. This is because sliding detector elements 184 move behind the collimator during the imaging operation to collect data at various points. This movement can be controlled by a motor such as the sweep motor 52 or additional motor installed. The organ or subject, such as a heart, could be centered in the middle of the detector head in an optimal scanning scenario. An effective field of view for such a system could be 36 by 20 centimeters. A quality field of view for such a system could be 20 by 20 centimeters. The installation information for this embodiment can include the number, location, and movement ability of each detector element. The detector head 180 is very useful in system installation configurations where the number of total detector columns is low, because each detector column would be able to handle more detection information. In this embodiment, the collimator could be attached to the detector head itself or individual detector elements. Thus, the movable detector elements 182 could have a collimator attached thereto so that a collimator would not have to be manufactured for the whole space, saving cost.

Figure 19:
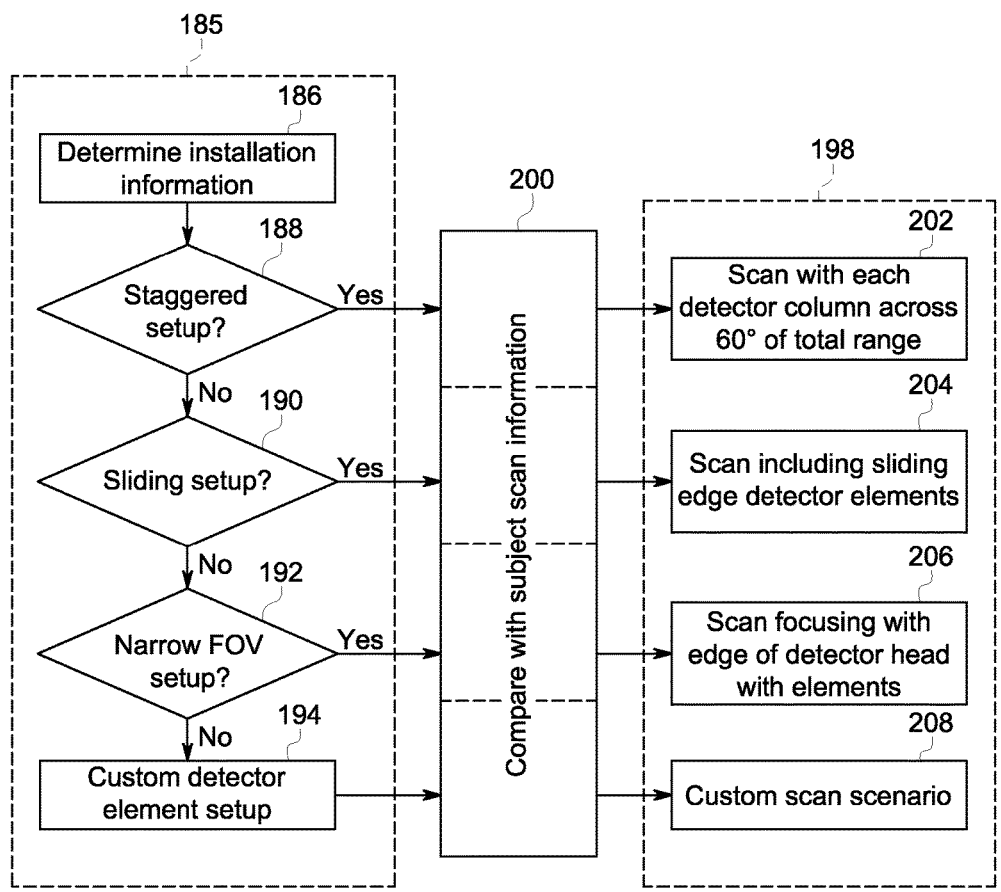
FIG. 19 is a flowchart of a method for controlling detector columns where detector elements are partially populated.

FIG. 19 is a flowchart of one embodiment in which different detector element configurations are applicable to the installation information. Dotted box 185 indicates that the steps 186-194 are examples of the types of determinations that could be made in step 80 of FIG. 8. Step 200 is an example of type of determination that could be made in step 82 of FIG. 8. And dotted box 198 indicates that the steps 202-208 are examples of the types of determinations that could be made in step 84 of FIG. 8.

In step 186, the system collects data from various parts of the overall system (such as shown in steps 71-75 of FIG. 8). Based on that data, the system determines whether the system has a staggered setup, in step 188, a sliding setup, in step 190, a narrow FOV setup, in step 192, or a custom detector element setup, in step 194. A staggered setup could be one such as demonstrated in FIGS. 17A and 17B. A sliding setup could be one such as demonstrated in FIG. 18. A narrow FOV setup could be one such as demonstrated in FIG. 16C.

In step 200, the system compares the determined detector element setup from the steps of dotted box 185 with subject scan information. This information is based on the subject of the scan (i.e. heart, thyroid, brain, breast, etc.) as well as the type of scan being performed.

In the steps of dotted box 198, an imaging operation is performed based on the installation information compared with the subject scan information. If there is a good fit between the installation information, the corresponding scan to the detector element is selected. This is indicated by the horizontal lines. Step 202 to scan with each detector column across sixty degrees of the total range (such as in FIGS. 20A-20C) is generally performed when the staggered setup is determined in step 188 and that matches well with the subject scan information. Step 204 to scan including sliding edge detector elements is generally performed when the sliding setup is determined in step 190 and that matches well with the subject scan information. Step 206 to scan focusing with edge of a detector head with installed elements is generally performed when the narrow FOV setup is determined in step 192 and that matches well with the subject scan information. Step 208 to scan using a custom scan scenario is generally performed when the installation setups do not match with the subject scan information or are not in any predefined arrangement.

Figure 20A:
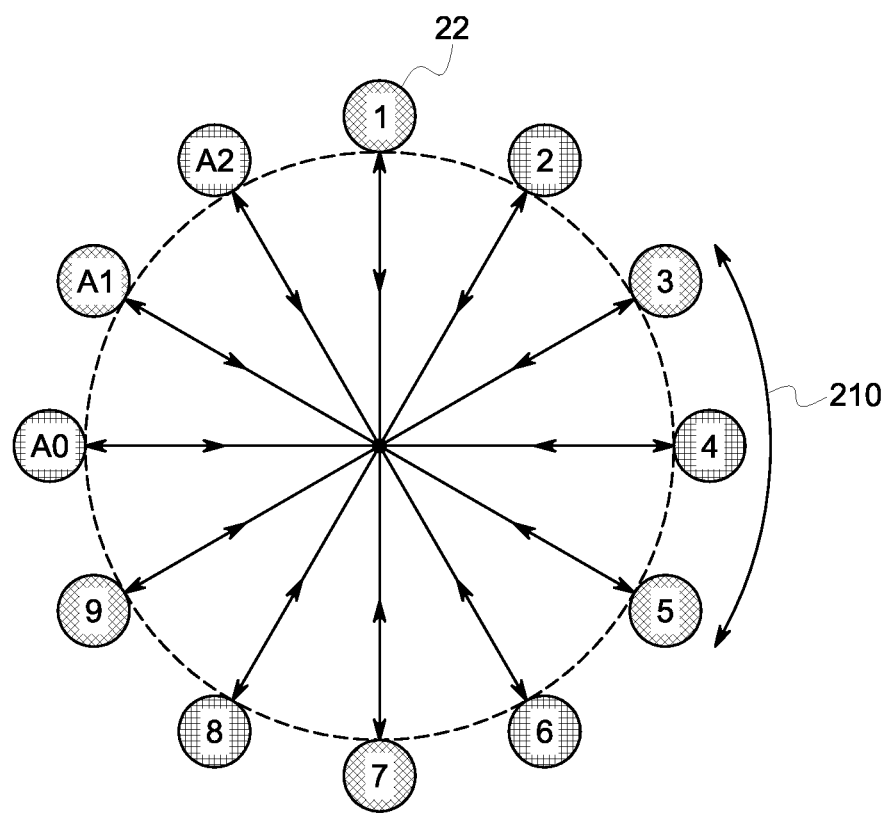
FIG. 20A is a radial construction view of a starting-position gantry system where detector elements are partially populated.
Figure 20B:
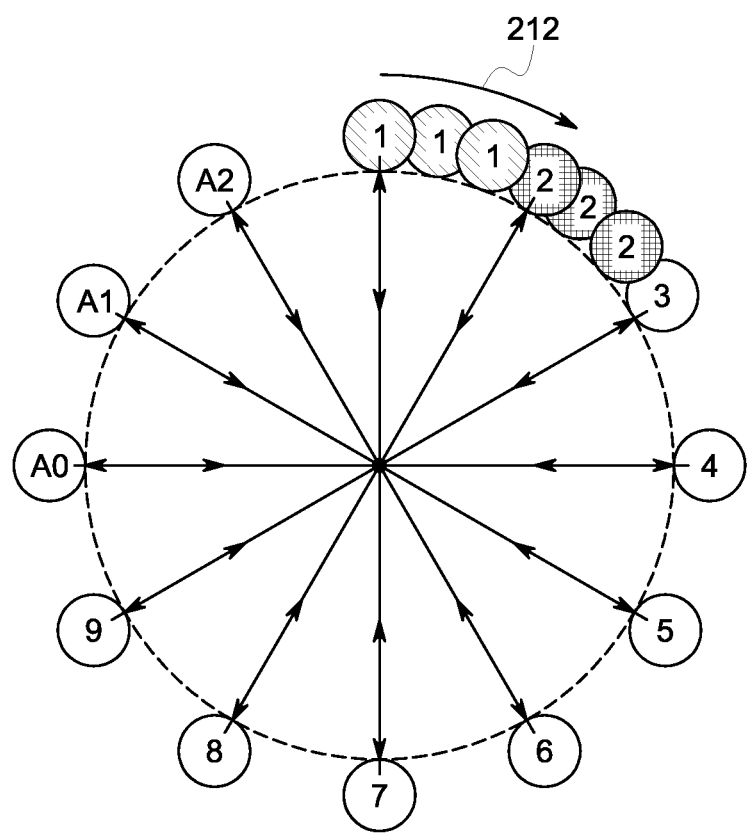
FIG. 20B is a radial construction view of moving detector columns in a gantry system where detector elements are partially populated.
Figure 20C:
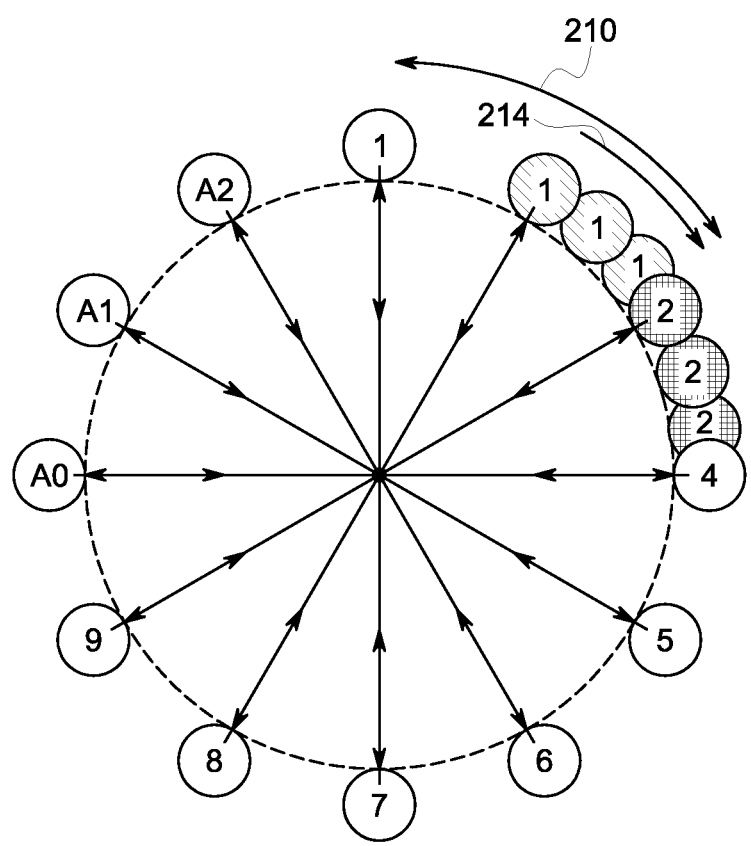
FIG. 20C is a radial construction view of moving detector columns in a gantry system where detector elements are partially populated.

FIGS. 20A-20C show the details of an imaging operation of step 202 where each detector column scans across sixty degrees across the total range. This could be best executed for a system of FIGS. 17A and 17B as discussed in detail above. Odd detector columns have odd detector elements installed and even detector columns have even detector elements installed. Therefore, to get a full scan of the subject, the system would have to orbitally rotate each detector column sixty degrees during the total imaging operation.

FIG. 20A shows a system with fully populated detector columns 22 with a gantry orbital rotation range 210 of sixty degrees. The detector arms can be extended radially in the system. While the detector columns are fully populated, the detector elements in each detector column are not, as discussed above.

FIG. 20B shows a staggered imaging operation during the first three movement locations, covering a gantry orbital rotation range 212 of thirty degrees.

FIG. 20C shows a staggered imaging operation during the final three movement locations, covering an additional gantry orbital rotation range 214 of thirty degrees. Thus, each angle of a scanning operation is covered by an even and an odd detector element. The imaging operation may take longer than a system with fully populated detector elements, but the system can be cheaper due to having only half of the total detector elements in the system.

As contemplated, the various embodiments provide a lower cost, upgradable, and customizable system for imaging operations. All functionality can be preserved, yet with a tradeoff of cost vs. acquisition time.

The configurable and controllable system of some embodiments could be controlled by user input. Thus, the user can override the automatic operation of the system and take full specific control of components of the system through a user interface.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a flash memory disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An imaging system, comprising:
   a gantry having a bore configured to accept a patient, the bore defining a circumference and a central axis extending along a center of the bore, the gantry configured to rotate about the center of the bore;
   between five and nine imaging detector columns attached to the gantry, each detector column comprising a detector arm and a detector head, each detector arm extending radially toward the center of the bore from the gantry, each detector head coupled to a corresponding detector arm and comprising at least one detector element, wherein each detector head is configured to be radially articulable toward and away from the center of the bore, and each detector head is configured to be pivotable with respect to the corresponding detector arm around a sweep pivot axis, each sweep pivot axis extending parallel to the central axis extending along the center of the bore; and
   at least one processor operably coupled to the detector columns and configured to independently control the between five and nine imaging detector columns, and to acquire imaging information with the detector elements, wherein the gantry includes additional gantry locations configured for installation of additional detector columns, the imaging system configured for the additional gantry locations to be vacant when the at least one processor acquires the imaging information with the between five and nine imaging detectors.

2. The imaging system of claim 1, wherein the imaging system comprises six or less imaging detector columns distributed along half or less of the circumference of the bore.

3. The imaging system of claim 1, wherein the detector heads of the between five and nine imaging detector columns are extendable toward the center of the bore toward a position in which the detector heads are adjacent each other.

4. The imaging system of claim 1, wherein the at least one processor is configured to acquire cardiac imaging information with the detector elements.

5. The imaging system of claim 1, wherein each detector head defines a length extending along the corresponding sweep pivot axis, wherein at least some of the detector heads include plural detector element locations extending along the length, each detector element location configured to accept a corresponding detector element, each detector element configured to receive photons during acquisition of imaging information.

6. The imaging system of claim 5, wherein the system is configured for vacant detector element locations and occupied detector element locations to alternate along the length of at least one of the detector heads.

7. The imaging system of claim 5, wherein the system is configured for all vacant detector element locations of at least one detector head to be positioned toward a first side of the detector head and all occupied detector element locations to be positioned toward an opposite side of the detector head.

8. The imaging system of claim 5, wherein detector element locations alternate between odd positions and even positions along the length, wherein the system is configured for a first detector head to comprise vacant detector element locations at the odd positions and occupied detector element location at the even positions, and for a second detector head adjacent the first detector head to comprise vacant detector element locations at the even positions and occupied detector element location at the odd positions.

9. An imaging system, comprising:
a gantry having a bore configured to accept a patient, the bore defining a circumference and a central axis extending along a center of the bore, the gantry configured to rotate about the center of the bore;
plural imaging detector columns attached to the gantry, each detector column comprising a detector arm and a detector head, each detector arm extending radially toward the center of the bore from the gantry, each detector head coupled to a corresponding detector arm and comprising at least one detector element, wherein each detector head is configured to be radially articulable toward and away from the center of the bore, and each detector head is configured to be pivotable with respect to the corresponding detector arm around a sweep pivot axis, each sweep pivot axis extending parallel to the central axis extending along the center of the bore, wherein each detector head defines a length extending along the corresponding sweep pivot axis, wherein at least some of the detector heads include plural detector element locations extending along the length, each detector element location configured to accept a corresponding detector element, each detector element configured to receive photons during acquisition of imaging information, wherein the system is configured for some of the detector element locations to be vacant during acquisition of imaging information; and
at least one processor operably coupled to the detector columns and configured to independently control the imaging detector columns, and to acquire imaging information with the detector elements.

10. The imaging system of claim 9, wherein the system is configured for vacant detector element locations and occupied detector element locations to alternate along the length of at least one of the detector heads.

11. The imaging system of claim 9, wherein the system is configured for all vacant detector element locations of at least one detector head to be positioned toward a first side of the detector head and all occupied detector element locations to be positioned toward an opposite side of the detector head.

12. The imaging system of claim 9, wherein detector element locations alternate between odd and even positions along the length, wherein the system is configured for a first detector head to comprise vacant detector element locations at the odd positions and occupied detector element location at the even positions, and for a second detector head adjacent the first detector head to comprise vacant detector element locations at the even positions and occupied detector element location at the odd positions.

13. A method comprising:
attaching between five and nine imaging detector columns to a gantry, the gantry having a bore configured to accept a patient, the bore defining a circumference and a central axis extending along a center of the bore, the gantry configured to rotate about the center of the bore, each detector column comprising a detector arm and a detector head, each detector arm extending radially toward the center of the bore from the gantry, each detector head coupled to a corresponding detector arm and comprising at least one detector element, wherein each detector head is configured to be radially articulable toward and away from the center of the bore, and each detector head is configured to be pivotable with respect to the corresponding detector arm around a sweep pivot axis, each sweep pivot axis extending parallel to the central axis extending along the center of the bore, wherein the detector columns are distributed along half or less of the circumference of the bore;
independently controlling, with at least one processor, the between five and nine imaging detector columns to acquire imaging information with the detector elements; and
reconstructing an image using the imaging information.

14. The method of claim 13, wherein attaching the between five and nine imaging detector columns comprises attaching six or less imaging detector columns.

15. The method of claim 13, wherein the imaging information is cardiac imaging information and the image is a cardiac diagnostic image.

16. The method of claim 13, wherein the gantry includes additional gantry locations configured for installation of additional detector columns, the method comprising leaving the additional gantry locations vacant when the at least one processor acquires the imaging information with the between five and nine imaging detectors.

17. The method of claim 13, wherein each detector head defines a length extending along the corresponding sweep pivot axis, wherein at least some of the detector heads include plural detector element locations extending along the length, each detector element location configured to accept a corresponding detector element, each detector element configured to receive photons during acquisition of imaging information, wherein the method comprises wherein leaving some of the detector element locations vacant during acquisition of imaging information.

18. The method of claim 13, wherein vacant detector element locations and occupied detector element locations alternate along the length of at least one of the detector heads.

* * * * *